(12) United States Patent
Pimentel et al.

(10) Patent No.: US 9,702,884 B2
(45) Date of Patent: Jul. 11, 2017

(54) METHODS FOR DETECTING THE PRESENCE OF IRRITABLE BOWEL SYNDROME AND SYSTEM FOR DIAGNOSING SAME

(71) Applicant: Cedars-Sinai Medical Center, Los Angeles, CA (US)

(72) Inventors: Mark Pimentel, Los Angeles, CA (US); Christopher Chang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/428,195

(22) PCT Filed: Aug. 19, 2013

(86) PCT No.: PCT/US2013/055626
§ 371 (c)(1),
(2) Date: Mar. 13, 2015

(87) PCT Pub. No.: WO2014/042828
PCT Pub. Date: Mar. 20, 2014

(65) Prior Publication Data
US 2015/0233944 A1  Aug. 20, 2015

Related U.S. Application Data

(60) Provisional application No. 61/701,923, filed on Sep. 17, 2012, provisional application No. 61/762,632, filed on Feb. 8, 2013.

(51) Int. Cl.
*G01N 33/68* (2006.01)
*A61K 38/17* (2006.01)

(52) U.S. Cl.
CPC ..... *G01N 33/6887* (2013.01); *A61K 38/1709* (2013.01); *G01N 2333/4703* (2013.01); *G01N 2800/06* (2013.01); *G01N 2800/065* (2013.01); *G01N 2800/2842* (2013.01)

(58) Field of Classification Search
CPC ....... G01N 33/6887; G01N 2333/4703; G01N 2800/06; G01N 2800/065; G01N 2800/2842; A61K 38/1709
See application file for complete search history.

(56) References Cited

U.S. PATENT DOCUMENTS

| | | | |
|---|---|---|---|
| 6,805,852 B2 | 10/2004 | Lin et al. | |
| 6,861,053 B1 | 3/2005 | Lin et al. | |
| 7,048,906 B2 | 5/2006 | Lin et al. | |
| 7,056,686 B2 | 6/2006 | Lin et al. | |
| 7,081,239 B2 | 7/2006 | Lin | |
| 7,244,412 B2 | 7/2007 | Lin | |
| 7,452,857 B2 | 11/2008 | Lin et al. | |
| 7,585,838 B2 | 9/2009 | Lin et al. | |
| 7,605,240 B2 | 10/2009 | Lin et al. | |
| 7,608,245 B2 | 10/2009 | Lin | |
| 7,615,207 B2 | 11/2009 | Lin | |
| 7,718,608 B2 | 5/2010 | Lin et al. | |
| 7,736,622 B2 | 6/2010 | Lin et al. | |
| 7,935,799 B2 | 5/2011 | Lin et al. | |
| 8,110,177 B2 | 2/2012 | Lin et al. | |
| 8,197,805 B2 | 6/2012 | Lin et al. | |
| 8,388,935 B2 | 3/2013 | Lin et al. | |
| 8,562,952 B2 | 10/2013 | Lin et al. | |
| 9,110,081 B2 | 8/2015 | Pimentel et al. | |
| 9,358,276 B2 | 6/2016 | Lin et al. | |
| 2003/0157159 A1 | 8/2003 | Franklin et al. | |
| 2004/0018528 A1 | 1/2004 | Morimoto et al. | |
| 2004/0106590 A1 | 6/2004 | Eisenstein | |
| 2006/0127359 A1 | 6/2006 | Borrelli | |
| 2006/0193871 A1 | 8/2006 | Lin | |
| 2007/0212691 A1 | 9/2007 | Yamasaki et al. | |
| 2009/0028940 A1 | 1/2009 | Jahagirdar et al. | |
| 2011/0183337 A1 | 7/2011 | Von Stein et al. | |
| 2011/0294726 A1 | 12/2011 | Pimentel et al. | |
| 2011/0305704 A1 | 12/2011 | Pimentel et al. | |
| 2012/0088257 A1 | 4/2012 | Mouthon et al. | |
| 2014/0206636 A1 | 7/2014 | Lin et al. | |
| 2016/0061837 A1 | 3/2016 | Pimentel et al. | |
| 2016/0103136 A1 | 4/2016 | Pimentel et al. | |
| 2017/0038393 A1 | 2/2017 | Pimentel et al. | |

FOREIGN PATENT DOCUMENTS

| | | |
|---|---|---|
| AU | 2002256254 B2 | 5/2007 |
| AU | 2007201246 A1 | 3/2009 |
| AU | 2010213773 | 10/2014 |
| AU | 2010213708 B2 | 12/2015 |

(Continued)

OTHER PUBLICATIONS

Carey MP, et al. BJU International. 86:970-976. 2000.*
Nemeth L, et al. Archives of Pathology & Laboratory Medicine. 126(6):692. Jun. 2002.*
European Application No. 13837424.4 Extended Search Report dated May 9, 2016; 8 pages.
PCT/US2014/059957 International Search Report and Written Opinion dated Jan. 8, 2015; 11 pages.

(Continued)

*Primary Examiner* — Robert Landsman
(74) *Attorney, Agent, or Firm* — Linda B. Huber; Nixon Peabody LLP

(57) ABSTRACT

Described herein are methods and systems for the detection of anti-vinculin antibodies, for determining a presence or likely presence of a gastrointestinal motility disorder, bladder motility disorder, or fibromyalgia. Further provided are methods of selecting and/or administering a therapy based on the presence or absence of anti-vinculin antibodies.

12 Claims, 19 Drawing Sheets

(56) References Cited

FOREIGN PATENT DOCUMENTS

| | | |
|---|---|---|
| CA | 2444548 C | 6/2016 |
| CL | 2011-1944 | 2/2012 |
| EP | 1 385 476 A | 2/2004 |
| EP | 2 261 665 B1 | 6/2004 |
| EP | 1 200 828 B1 | 10/2007 |
| EP | 2 261 664 A2 | 12/2010 |
| EP | 2 267 445 A1 | 12/2010 |
| EP | 2 305 213 A2 | 4/2011 |
| EP | 1 811 303 B1 | 6/2011 |
| EP | 2 396 029 | 12/2011 |
| EP | 2 370 435 B1 | 1/2015 |
| EP | 2 256 498 B1 | 4/2015 |
| EP | 2895856 | 7/2015 |
| EP | 2267445 B1 | 8/2016 |
| JP | 2009-102401 | 5/2009 |
| JP | 4653936 | 12/2010 |
| JP | 2017502253 A | 1/2017 |
| WO | WO 92/06690 A1 | 4/1992 |
| WO | 0111334 A2 | 2/2001 |
| WO | WO 01/11077 A2 | 2/2001 |
| WO | WO 02/083926 A2 | 10/2002 |
| WO | WO 2004/024097 A2 | 3/2004 |
| WO | WO 2006/102536 A2 | 9/2006 |
| WO | WO 2008/016708 A2 | 2/2008 |
| WO | WO 2009/108814 A1 | 9/2009 |
| WO | WO 2010/093776 A1 | 8/2010 |
| WO | WO 2010/093801 A1 | 8/2010 |
| WO | WO 2012/007913 A2 | 1/2012 |
| WO | WO 2014/042828 A2 | 3/2014 |
| WO | 2015054529 A1 | 4/2015 |
| WO | 2016057772 A1 | 4/2016 |

OTHER PUBLICATIONS

PCT/US2015/054655 International Search Report and Written Opinion dated Feb. 12, 2016; 7 pages.

Morales et al. Tu2056 Antibodies to Cytolethal Distending Toxin B and Auto-Antibodies to Human Vinculin are Elevated in IBS Subjects. Gastroenterology (2013). 144(5): Suppl. 1, p. S-914.

Nelson et al. Vinculin Activators Target Integrins from within the Cell to Increase Melanoma Sensitivity to Chemotherapy. Molecular Cancer Research (2011). 9(6):1-12.

Nemeth et al. Altered Cytoskeleton in Smooth Muscle of Aganglionic Bowel. Arch Pathol Lab Med (2002). 126:692-696.

Novak, K. A Serologic Test for Irritable Bowel Syndrome and Other News from ACG. Gastroenterology Press Highlights (2013); pp. 1-2. Retrieved from: <www.gastrojournal.org/pb/assets/raw/Health%20Advance/journals/ygast/November26_PressHighlight3.pdf> on Feb. 3, 2016.

Pimentel et al. Development and Validation of a Biomarker for Diarrhea-Predominant Irritable Bowel Syndrome in Human Subjects. PLoS One (2015). 10(5): pp. 1-12.

Rolle et al. Structural basis of voiding dysfunction in megacystis microcolon intestinal hypoperistalsis syndrome. Journal of Pediatric Urology (2006). 2:277-284.

Turkay et al. Noninvasive Methods in Evaluation of Inflammatory Bowel Disease: Where Do We Stand Now? An Update. Clinics (2010). 65(2):221-31.

PCT/US2013/005626 International Search Report and Written Opinion dated Aug. 18, 2014; 14 pages.

PCT/US2013/005626 International Preliminary Report on Patentability dated Aug. 18, 2014; 12 pages.

PCT/US2010/023873 International Search Report and Written Opinion dated Apr. 1, 2010; 7 pages.

PCT/US2010/023873 International Preliminary Report on Patentability dated Aug. 16, 2011; 6 pages.

PCT/US2010/023911 International Search Report and Written Opinion dated May 14, 2010; 11 pages.

PCT/US2010/023911 International Preliminary Report on Patentability dated Aug. 16, 2011; 8 pages.

EP Application No. 10741713.1 Extended Search Report dated Jul. 27, 2012; 16 pages.

EP Application No. 10741728.9 Extended Search Report dated Oct. 17, 2014; 7 pages.

American College of Gastroenterology Task Force on IBS. An Evidence-Based Position Statement on the Management of Irritable Bowel Syndrome. The American Journal of Gastroenterology (2009). 104(S1): S1-35.

Abuoun et al. Cytolethal Distending Toxin (CDT)—Negative and Campylobacter jejuni Strains Anti-CDT Neutralizing Antibodies are Induced during Human Infection but Not during Colonization in Chickens. Infection and Immunity (2005). 73(5): 3053-3062.

Bourke, B. Campylobacter infection: small bowel and colon. Current Opinion in Gastroenterology. (2002). 18:4-9.

Cambridge et al. Anti-neutrophil antibodies in inflammatory bowel disease: prevalence and diagnostic role. Gut (2013). 33:668-674.

Connor, B. Sequelae of Traveler's Diarrhea: Focus on Postinfectious Irritable Bowel Syndrome. Clinical Infectious Diseases (2005). 41(suppl 3):5577-5586.

Dunlop et al. Relative Importance of Enterochromaffin Cell Hyperplasia, Anxiety, and Depression in Postinfectious IBS. Gastroenterology (2003). 125:1651-1659.

Dupont, A. et al. Travelers' Diarrhea: Modern Concepts and New Developments. Current Treatment Option in Gastroenterology. Database Medline: US National Library of Medicine. (2006). Abstract Only.

Dupont, H. Postinfectious Irritable Bowel Syndrome: Clinical Aspects, Pathophysiology, and Treatment. Practical Gastroenterology (2007). 31(S9): 18-24.

Fox et al. Gastroenteritis in NF-kappaB-deficient mice is produced with wildtype Camplyobacter jejuni but not with C. jejuni lacking cytolethal distending toxin despite persistent colonization with both strains. Infection & Immunity (2004). 72(2):1116-25.

Halsey, J. Current and Future Treatment Modalities for Clostridium-difficile-Associated Disease. Am J. Health-Syst Pharm (2008). 65:705-715.

Hickey et al. Campylobacter jejuni Cytolethal Distending Interleukin-8 from Intestinal Epithelial Cells. Infection Toxin Mediates Release of and Immunity (2000). 68(12):6535-6541.

Jee et al. Antibotics and Cdt Expression in Campylobacter Jejuni Contribute to Duration of Colonization in Rats. Gastroenterology. (2008). 134(4). Abstract Only.

Johnson et al. Interruption of Recurrent Clostridium difficle-Associated Diarrhea Episodes by Serial Therapy with Vancomycin and Rifaximin. Clinical Infectious Diseases (2007). 44:846-848.

Kokkotou et al. Comparative Efficacies of Rifaximin and Vancomycin for Treatment of Clostridium difficile-Associated Diarrhea and Prevention of Disease Recurrence in Hamsters. Antimicrobial Agents and Chemotherapy (2008). 52(3): 1121-1126.

Medindia. IBS Sufferers Benefited by Non-Absorbable Antibiotics. (2006). Retrieved from Internet: www.medindia.net/news/view_newsmain.asp?x=15225.

Morales et al. Antibodies to Cytolethal Distending Toxin of Campylobacter Jejuni Bind to Enteric Neuronal Elements: Further Evidence for Molecular Mimicry. Gastroenterology (2012). 142(5): Suppl 1.

Moss-Morris et al. To "Lump" or to "Split" the Functional Somatic Syndromes: Can Infections and Emotional Risk Factors Differentiate between the Onset of Chronic Fatigue Syndrome and Irritable Bowel Syndrome. Psychosomatic Medicine (2006). 68:463-469.

Neal et al. Prevalence of Gastrointestinal Symptoms Six Months after Bacterial Gastroenteritis and Risk Factors for Development of the Irritable Bowel Syndrome: Postal Survey of Patients. BMJ (1997). 314:779, 14 pages.

Peng et al. a-Catenin Uses a Novel Mechanism to Activate Vinculin. The Journal of Biological Chemistry (2012). 287(10): 7728-7737.

Pimentel et al. A New Rat Model Links Two Complementary Theories in Irritable Bowel Syndrome. Digestive Diseases and Sciences (2007). 53(4):982-989.

Purdy et a. Characterisation of cytolethal distending toxin (CDT) mutants of Campylobacter jejuni. J. Med. Microbiol. (2000). 49: pp. 473-479.

(56) References Cited

OTHER PUBLICATIONS

Sabato et al. A New Variant of Food Poisoning: Enteroinvasive Klebsiella Pneumoniae and *Escherichia coli* Sepsis from a Contaminated Hamburger. The American Journal of Gastroenterology (1998). 93(1): 118-119.
Science Daily. Irritable Bowel Syndrome Study Shows that Targeted Antibiotics Lead to Long-Lasting Improvement in Symptoms. (2005). Retrieved from Internet: http://www.sciencedaily.com/releases/2005/11/051109181127.htm.
Spiller et al. Increased rectal mucosal enteroendocrine cells, T lymphocytes, and increased gut permeability following acute Campylobacter enteritis and inpost-dysenteric irritable bowel syndrome. Gut (2000). 47:804-811.
Suh et al. Patients with irritable bowel syndrome or constipation have an increased risk for ischaemic colitis. Alimentary Pharmacology & Therapeutics (2007). 25:681-692.
Sung et al. Antibody to Cytolethal Distending Toxin of Campylobacter Jejuni Stains Small Bowel Myenteric Neuromuscular Elements in Control and C. Jejuni Exposed Rats: A Possible Role of Molecular Mimicry. Gastroenterology (2010). 138(5). p. S-770.
Taylor et al. Rifaximin, a Nonabsorbed Oral Antibiotic, Prevents Shigellosis after Experimental Challenge. Clinical Infectious Diseases. (2006). 42:1283-1288.
The Free Dictionary. Definition of Mitigation by the Free Online Dictionary, Thesaurus and Encyclopedia. Retrieved from: www.thefreedictionary.com/p/mitigation on Nov. 19, 2013.
Morales et al. Antibodies to an 18-Residue Peptide of Cdt are Found in the Serum of Rats in a Model of Post-Infectious IBS. Gastroenterology (2011). 140(5), p. S-371.
Morales et al. Effect of Rifaximin Treatment on Anti-Vinculin Antibodies in IBS with Diarrhea. Gastroenterology (2016).150(4). Supplement 1. p. S-695.
Rezaie et al. Assessment of Anti-Vinculin and Anti-CdtB Antibodies in IBS Subtypes. Gastroenterology (2016).150(4). Supplement 1. p. S62.
EP Application No. 14851688.3 Extended Search Report dated Mar. 10, 2017; 10 pages.
Lembo et al. Use of serum biomarkers in a diagnostic test for irritable bowel syndrome. Alimentary Pharmacology & Therapeutics (2009). 29:834-842.
Pimentel et al. Anti-vinculin antibodies: Multicenter validation of a diagnostic blood test for irritable bowel syndrome. The American Journal of Gastroenterology (2013). 108:1887; p. S571. Abstract Only.
Pimentel et al. Autoimmunity to vinculin in humans may be important in the pathophysiology of IBS. Gastroenterology (2014). 146(5); suppl 1, Su2020. Abstract Only.
Triantafyllou et al. Evaluating the Role of Cytolethal Distending Toxin in the Development of Small Intestinal Bacterial Overgrowth in a Rat Model Post-Infectious IBS. Gastroenterology (2014). 146(5): suppl 1, Su1424. Abtract Only.

\* cited by examiner

SEQUENCE LISTING

```
<160> NUMBER OF SEQ ID NOS: 6

<210> SEQ ID NO 1
<211> LENGTH: 1066
<212> TYPE: PRT
<213> ORGANISM: Homo sapiens

<400> SEQUENCE: 1

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
```

```
                245                 250                 255
Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
            325                 330                 335

Asp Leu Arg Ala Arg Gly Gln Gly Ser Ser Pro Val Ala Met Gln Lys
        340                 345                 350

Ala Gln Gln Val Ser Gln Gly Leu Asp Val Leu Thr Ala Lys Val Glu
    355                 360                 365

Asn Ala Ala Arg Lys Leu Glu Ala Met Thr Asn Ser Lys Gln Ser Ile
370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
            405                 410                 415

Lys Ile Ala Glu Leu Cys Asp Asp Pro Lys Glu Arg Asp Asp Ile Leu
        420                 425                 430

Arg Ser Leu Gly Glu Ile Ser Ala Leu Thr Ser Lys Leu Ala Asp Leu
    435                 440                 445

Arg Arg Gln Gly Lys Gly Asp Ser Pro Glu Ala Arg Ala Leu Ala Lys
        450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
            485                 490                 495

Ile Glu Gln Ala Gln Arg Trp Ile Asp Asn Pro Thr Val Asp Asp Arg
        500                 505                 510

Gly Val Gly Gln Ala Ala Ile Arg Gly Leu Val Ala Glu Gly His Arg
    515                 520                 525

Leu Ala Asn Val Met Met Gly Pro Tyr Arg Gln Asp Leu Leu Ala Lys
        530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
            565                 570                 575

Gln Asp Ser Leu Lys Asp Leu Lys Ala Arg Met Gln Glu Ala Met Thr
        580                 585                 590

Gln Glu Val Ser Asp Val Phe Ser Asp Thr Thr Thr Pro Ile Lys Leu
    595                 600                 605

Leu Ala Val Ala Ala Thr Ala Pro Pro Asp Ala Pro Asn Arg Glu Glu
610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Val Gly Thr Ala Asn Lys Ser
            645                 650                 655

Thr Val Glu Gly Ile Gln Ala Ser Val Lys Thr Ala Arg Glu Leu Thr
        660                 665                 670
```

-continued

Pro Gln Val Val Ser Ala Ala Arg Ile Leu Leu Arg Asn Pro Gly Asn
            675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765

Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
    835                 840                 845

Leu Glu Gln Leu Arg Leu Thr Asp Glu Leu Ala Pro Pro Lys Pro Pro
850                 855                 860

Leu Pro Glu Gly Glu Val Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Gly Asn Asp Ile Ile Ala Ala Ala Lys Arg Met Ala Leu
    915                 920                 925

Leu Met Ala Glu Met Ser Arg Leu Val Arg Gly Gly Ser Gly Thr Lys
930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
                965                 970                 975

Ile Arg Thr Asn Leu Leu Gln Val Cys Glu Arg Ile Pro Thr Ile Ser
            980                 985                 990

Thr Gln Leu Lys Ile Leu Ser Thr Val Lys Ala Thr Met Leu Gly Arg
    995                 1000                1005

Thr Asn Ile Ser Asp Glu Glu Ser Glu Gln Ala Thr Glu Met Leu
    1010                1015                1020

Val His Asn Ala Gln Asn Leu Met Gln Ser Val Lys Glu Thr Val
    1025                1030                1035

Arg Glu Ala Glu Ala Ala Ser Ile Lys Ile Arg Thr Asp Ala Gly
    1040                1045                1050

Phe Thr Leu Arg Trp Val Arg Lys Thr Pro Trp Tyr Gln
    1055                1060                1065

<210> SEQ ID NO 2
<211> LENGTH: 23

<212> TYPE: DNA
<213> ORGANISM: Artificial Sequence
<220> FEATURE:
<223> OTHER INFORMATION: synthetic construct

<400> SEQUENCE: 2
ggagattact gccctggctc cta                                           23

<210> SEQ ID NO 3
<211> LENGTH: 24
<212> TYPE: DNA
<213> ORGANISM: Artificial Sequence
<220> FEATURE:
<223> OTHER INFORMATION: synthetic construct

<400> SEQUENCE: 3
gactcatcgt actcctgctt gctg                                          24

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
gccaagcagt gcacagataa                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic construct

<400> SEQUENCE: 5
tctttctaac ccagcgcagt                                               20

<210> SEQ ID NO 6
<211> LENGTH: 633
<212> TYPE: PRT
<213> ORGANISM: Shigella

<400> SEQUENCE: 6

Met His Asn Val Asn Asn Thr Gln Ala Pro Thr Phe Leu Tyr Lys Ala
1               5                   10                  15

Thr Ser Pro Ser Ser Thr Glu Tyr Ser Glu Leu Lys Ser Lys Ile Ser
            20                  25                  30

Asp Ile His Ser Ser Gln Thr Ser Leu Lys Thr Pro Ala Ser Val Ser
        35                  40                  45

Glu Lys Glu Asn Phe Ala Thr Ser Phe Asn Gln Lys Cys Leu Asp Phe
    50                  55                  60

Leu Phe Ser Ser Gly Lys Glu Asp Val Leu Arg Ser Ile Tyr Ser
65                  70                  75                  80

Asn Ser Met Asn Ala Tyr Ala Lys Ser Glu Ile Leu Glu Phe Ser Asn
                85                  90                  95

Val Leu Tyr Ser Leu Val His Gln Asn Gly Leu Asn Phe Glu Asn Glu
            100                 105                 110

Lys Gly Leu Gln Lys Ile Val Ala Gln Tyr Ser Glu Leu Ile Ile Lys
        115                 120                 125

Asp Lys Leu Ser Gln Asp Ser Ala Phe Gly Pro Trp Ser Ala Lys Asn
    130                 135                 140

-continued

Lys Lys Leu His Gln Leu Arg Gln Asn Ile Glu His Arg Leu Ala Leu
145                 150                 155                 160

Leu Ala Gln Gln His Thr Ser Gly Glu Ala Leu Ser Leu Gly Gln Lys
            165                 170                 175

Leu Leu Asn Thr Glu Val Ser Ser Phe Ile Lys Asn Asn Ile Leu Ala
            180                 185                 190

Glu Leu Lys Leu Ser Asn Glu Thr Val Ser Ser Leu Lys Leu Asp Asp
            195                 200                 205

Leu Val Asp Ala Gln Ala Lys Leu Ala Phe Asp Ser Leu Arg Asn Gln
210                 215                 220

Arg Lys Asn Thr Ile Asp Ser Lys Gly Phe Gly Ile Gly Lys Leu Ser
225                 230                 235                 240

Arg Asp Leu Asn Thr Val Ala Val Phe Pro Glu Leu Leu Arg Lys Val
            245                 250                 255

Leu Asn Asp Ile Leu Glu Asp Ile Lys Asp Ser His Pro Ile Gln Asp
            260                 265                 270

Gly Leu Pro Thr Pro Glu Asp Met Pro Asp Gly Gly Pro Thr Pro
            275                 280                 285

Gly Ala Asn Glu Lys Thr Ser Gln Pro Val Ile His Tyr His Ile Asn
290                 295                 300

Asn Asp Asn Arg Thr Tyr Asp Asn Arg Val Phe Asp Asn Arg Val Tyr
305                 310                 315                 320

Asp Asn Ser Tyr His Glu Asn Pro Glu Asn Asp Ala Gln Ser Pro Thr
            325                 330                 335

Ser Gln Thr Asn Asp Leu Leu Ser Arg Asn Gly Asn Ser Leu Leu Asn
            340                 345                 350

Pro Gln Arg Ala Leu Val Gln Lys Val Thr Ser Val Leu Pro His Ser
            355                 360                 365

Ile Ser Asp Thr Val Gln Thr Phe Ala Asn Asn Ser Ala Leu Glu Lys
370                 375                 380

Val Phe Asn His Thr Pro Asp Asn Ser Asp Gly Ile Gly Ser Asp Leu
385                 390                 395                 400

Leu Thr Thr Ser Ser Gln Glu Arg Ser Ala Asn Asn Ser Leu Ser Arg
            405                 410                 415

Gly His Arg Pro Leu Asn Ile Gln Asn Ser Ser Thr Thr Pro Pro Leu
            420                 425                 430

His Pro Glu Gly Val Thr Ser Ser Asn Asp Asn Ser Ser Asp Thr Thr
            435                 440                 445

Lys Ser Ser Ala Ser Leu Ser His Arg Val Ala Ser Gln Ile Asn Lys
            450                 455                 460

Phe Asn Ser Asn Thr Asp Ser Lys Val Leu Gln Thr Asp Phe Leu Ser
465                 470                 475                 480

Arg Asn Gly Asp Thr Tyr Leu Thr Arg Glu Thr Ile Phe Glu Ala Ser
            485                 490                 495

Lys Lys Val Thr Asn Ser Leu Ser Asn Leu Ile Ser Leu Ile Gly Thr
            500                 505                 510

Lys Ser Gly Thr Gln Glu Arg Glu Leu Gln Glu Lys Ser Lys Asp Ile
            515                 520                 525

Thr Lys Ser Thr Thr Glu His Arg Ile Asn Asn Lys Leu Lys Val Thr
            530                 535                 540

Asp Ala Asn Ile Arg Asn Tyr Val Thr Glu Thr Asn Ala Asp Thr Ile
545                 550                 555                 560

-continued

```
Asp Lys Asn His Ala Ile Tyr Glu Lys Ala Lys Glu Val Ser Ser Ala
            565                 570                 575

Leu Ser Lys Val Leu Ser Lys Ile Asp Asp Thr Ser Ala Glu Leu Leu
            580                 585                 590

Thr Asp Asp Ile Ser Asp Leu Lys Asn Asn Asn Asp Ile Thr Ala Glu
            595                 600                 605

Asn Asn Asn Ile Tyr Lys Ala Ala Lys Asp Val Thr Thr Ser Leu Ser
            610                 615                 620

Lys Val Leu Lys Asn Ile Asn Lys Asp
625                 630
```

US 9,702,884 B2

METHODS FOR DETECTING THE PRESENCE OF IRRITABLE BOWEL SYNDROME AND SYSTEM FOR DIAGNOSING SAME

CROSS-REFERENCE TO RELATED APPLICATIONS

This application is a National Phase of International Application No. PCT/US2013/055626, filed Aug. 19, 2013, which designated the U.S. and that International Application was published under PCT Article 21(2) in English. This application also includes a claim of priority under 35 U.S.C. §119(e) to U.S. provisional patent application No. 61/762,632, filed Feb. 8, 2013 and U.S. provisional patent application No. 61/701,923 filed Sep. 17, 2012, the entirety of which is hereby incorporated by reference.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Irritable bowel syndrome (IBS) is the most common functional gastrointestinal disorder. While the pathogenesis has historically focused on visceral hyperalgesia (1), recent work points to the pathophysiology of IBS being due to aberrations in gut flora. These hypotheses have emerged from two distinct areas of research. The first gut flora hypothesis is that small intestinal bacterial overgrowth (SIBO) may contribute to IBS and its symptoms. In a recent paper (2), Koch's postulates suggest that the evidence underpins this concept. This is further supported by recent phase III success of antibiotics in treating IBS (3) and culture studies of the proximal small bowel (Posserud and Pyleris studies). The other gut flora hypothesis is based on the development of IBS after an acute episode of gastroenteritis. There are now two meta-analyses, both of which reveal a similar finding that approximately 10% of subjects presenting with acute gastroenteritis will develop IBS long term (4, 5).

Many treatment methods of the prior art focuses on the relief of symptoms. Accordingly, there is a need in the art for additional methods of diagnosing and treating IBS, particularly treating the cause of IBS, as well as treating motility disorders of the gut and the bladder.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method, comprising: providing a biological sample from a subject desiring diagnosis of a gastrointestinal motility disorder, bladder motility disorder, or fibromyalgia; detecting in the biological sample, a presence or a level of an anti-vinculin antibody; and determining a presence or likely presence of the gastrointestinal motility disorder, bladder motility disorder, or fibromyalgia if the presence of the anti-vinculin antibody is detected, if the level of the anti-vinculin antibody is higher than an established control level, or if the level of the anti-vinculin antibody is significantly higher than an established control level, or determining an absence or likely absence of the gastrointestinal motility disorder, bladder motility disorder, or fibromyalgia if an absence of the anti-vinculin antibody is detected, if the level of the anti-vinculin antibody is equal to or lower than an established control level, or if the level of the anti-vinculin antibody is not significantly higher than an established control level.

In various embodiments, the method can further comprise selecting a therapy for the gastrointestinal motility disorder, bladder motility disorder, or fibromyalgia if the presence or likely presence of the gastrointestinal motility disorder, bladder motility disorder, or fibromyalgia is determined.

In various embodiments, the therapy can be a course of antibiotic therapy. In various embodiments, the therapy can comprise an anti-vinculin antibody neutralizing agent or an anti-vinculin antibody inhibiting agent. In various embodiments, the therapy can comprise an agent to change vinculin from an inactive state to an active state. In various embodiments, the therapy can comprise a vinculin agonist. In various embodiments, the vinculin agonist can be a vinculin activating peptide. In various embodiments, the therapy can comprise a vinculin activator. In various embodiments, the vinculin activator can be talin, f-actin, a-catenin or a combination thereof.

In various embodiments, the method can further comprise administering the therapy.

Various embodiments of the present invention provide for a system, comprising: an isolated biological sample from a subject desiring diagnosis of a gastrointestinal motility disorder, bladder motility disorder, or fibromyalgia; and an assay for detecting in the biological sample, a presence of an anti-vinculin antibody.

In various embodiments, the assay can be an enzyme-linked immunosorbent assay (ELISA), wherein the ELISA comprises using vinculin, SEQ ID NO:1 or a fragment thereof as a substrate or reagent to bind the anti-vinculin antibody.

Various embodiments of the present invention provide for a method, comprising: providing a biological sample from a subject desiring diagnosis of a gastrointestinal motility disorder, bladder motility disorder, or fibromyalgia; detecting in the biological same, a presence or a level of an anti-vinculin antibody; and determining a presence or likely presence of irritable bowel syndrome (IBS) if the presence of the anti-vinculin antibody is detected, if the level of the anti-vinculin antibody is higher than an established control level, or if the level of the anti-vinculin antibody is significantly higher than an established control level, or determining an presence or likely presence of inflammatory bowel disease (IBD) if an absence of the anti-vinculin antibody is detected, if the level of the anti-vinculin antibody is equal to or lower than an established control level, or if the level of the anti-vinculin antibody is not significantly higher than an established control level.

In various embodiments, the method can further comprise selecting an IBS therapy if IBS is diagnosed, or selecting an IBD therapy if IBD is diagnosed. In various embodiments, the IBS therapy can be a course of antibiotic therapy. In various embodiments, the IBS therapy can comprise an anti-vinculin antibody neutralizing agent or an anti-vinculin antibody inhibiting agent. In various embodiments, the IBS therapy can comprise an agent to change vinculin from an inactive state to an active state. In various embodiments, the IBS therapy can comprise a vinculin agonist. In various embodiments, the vinculin agonist can be a vinculin activating peptide. In various embodiments, the IBS therapy can comprise a vinculin activator. In various embodiments, the vinculin activator can be talin, f-actin, a-catenin or a combination thereof.

In various embodiments, the method can further comprise administering the IBS therapy or the IBD therapy.

Various embodiments of the present invention provide for a system, comprising: an isolated biological sample from a subject desiring a diagnosis to distinguish between irritable bowel syndrome (IBS) and inflammatory bowel disease (IBD); and an assay for detecting in the biological sample, a presence of an anti-vinculin antibody.

In various embodiments, the assay can be an enzyme-linked immunosorbent assay (ELISA), wherein the ELISA comprises using vinculin, SEQ ID NO:1 or a fragment thereof as a substrate or reagent to bind the anti-vinculin antibody.

Various embodiments of the present invention provide for a method, comprising: providing an therapy agent selected from the group consisting of: an anti-vinculin antibody neutralizing agent, an anti-vinculin antibody inhibiting agent, an agent capable of changing vinculin from an inactive state to an active state, a vinculin agonist, a vinculin activator, and combinations thereof; and administering the therapy agent to a subject desiring treatment of a gastrointestinal motility disorder, bladder motility disorder, or fibromyalgia to treat the gastrointestinal motility disorder, bladder motility disorder, or fibromyalgia.

In various embodiments, the vinculin agonist can be a vinculin activating peptide. In various embodiments, the vinculin activator can be talin, f-actin, a-catenin or a combination thereof.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
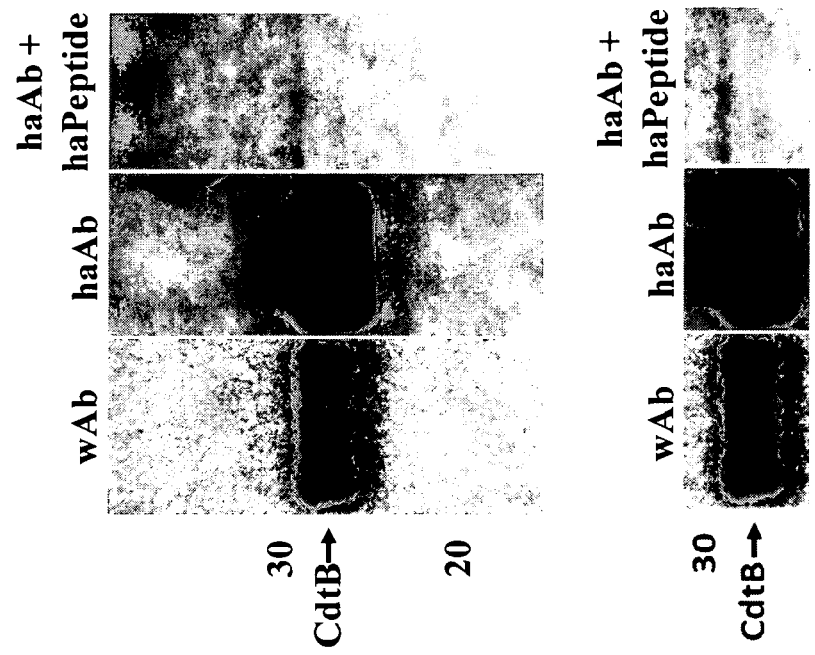
FIG. 1 depicts Western blot of protein vs. antibody in accordance with various embodiments of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. For references on how to prepare these antibodies, see D. Lane, *Antibodies: A Laboratory Manual* (Cold Spring Harbor Press, Cold Spring Harbor N.Y., 1988); Kohler and Milstein, (1976) Eur. J. Immunol. 6: 511; Queen et al. U.S. Pat. No. 5,585,089; and Riechmann et al., Nature 332: 323 (1988).

One skilled in the art will recognize many methods and materials similar or equivalent to those described herein, which could be used in the practice of the present invention. Indeed, the present invention is in no way limited to the methods and materials described.

"Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"Significantly higher" as used herein relating to reference amounts refers to a statistically significant amount higher than the reference amount.

Our discovery of the cross reactivity of CdtB antibodies with endogenous factors in uninfected rat ileal tissue by immunohistochemistry led to the study of susceptibility to development of IBS via CdtB molecular mimicry as a mechanism in the development of bacterial overgrowth. In this study, we investigated the immune response associated with CdtB in animal and human systems by tracking antibodies that bind CdtB during acute infection and the development of CdtB-associated antibodies as a predictor of IBS in both rats and humans.

Antibodies to cdtB after acute gastroenteritis through molecular mimicry produce an autoantibody to vinculin in IBS. Detection of this antibody is predictive of IBS over IBD and healthy controls. In animals, we have shown that titers of anti-cdtB correlate with the degree of bacterial overgrowth, and without wishing to be bound by any particular theory, we believe that a neuropathy induced by these antibodies is a cause of SIBO.

We demonstrate for the first time that molecular mimicry through autoimmunity may have an important role in the pathophysiology of post-infectious IBS in both rats and humans. Antibodies to cytolethal distending toxin B subunit of C. jejuni cross react with elements of the enteric nervous system and specifically ICC and myenteric ganglia. This interaction appears to create a degree of cellular inflammation and perhaps through effects on gut motor activity, small intestinal bacterial overgrowth since greater antibody titers were predictive of greater abnormalities in small bowel flora. Furthermore, detection of these antibodies in the serum of humans and rats have important diagnostic value.

It has become clear that acute gastroenteritis is a cause of irritable bowel syndrome. From two recent meta-analyses, the incidence of IBS after an outbreak of bacterial gastroenteritis is approximately 10% (Thabane and Halvorsson studies). Two important outbreaks have been most studied including the Walkerton outbreak from Canada and the outbreak in Spain (Mearin et al.). Prior to these studies, investigators had suggested that post-infectious IBS was either a separate entity or a small subset of the total IBS population. However, a recent model using military and the known prospective data on post-infectious IBS combined with CDC data on the incidence of gastroenteritis in the US, now suggests that more than 9% of the entire US population would have IBS from this cause. While modeling can be difficult it at least suggests that acute gastroenteritis could be responsible for a large portion of IBS in the community and may be the major cause.

There have been a number of physiologic observations in subjects with IBS. These include demonstration of visceral hypersensitivity. While many suggest that visceral sensitivity is the basis for the Rome criteria in IBS, ironically, bloating is often noted as the most bothersome symptom in patient study. Based on this symptom, over a decade ago, studies began to suggest that small intestinal bacterial overgrowth (SIBO) may be a feature of IBS. While this concept was initially controversial, two recent large scale studies have confirmed an excess of coliform bacteria in the small intestine of IBS compared to healthy controls (Posserud) and even compared to subjects with other foregut disease (Pyleris). In fact, in subjects with diarrhea predominant IBS, 60% of subjects had culture proven SIBO (Pyleris).

Numerous animal models have been created to study post-infectious IBS. However, some of the more prominently published models have used pathogens that are an uncommon pathogen in IBS and the focus of these models has been the development of visceral hyperalgesia. The most common cause of bacterial gastroenteritis in the US is Campylobacter jejuni and thus, is likely the greatest contributor to the overall incidence of post-infectious IBS in the US. Using this pathogen, a recent rodent model has demonstrated development of altered bowel form, SIBO, reduced ICC and increased intrarectal lymphocytes. These findings mimic the findings in humans with IBS and post-infectious IBS.

While C. jejuni is a common cause of gastroenteritis and important cause of post-infectious IBS, multiple bacterial pathogens have been incriminated in the development of IBS. This suggests either a common host response to this infection or a common toxin. Cytolethal distending toxin is common to almost all bacterial causes of acute gastroenteritis. This toxin has three components (Cdt A, B and C). However, the active toxin is believed to be Cdt B based on in vitro study of effect on HeLa cells. In the rodent model described above, infection of rats with C. jejuni 81-176 with an insertion deletion of CdtB did not result in the full phenotype of post-infectious IBS. Although human studies suggested that the intensity of the acute gastroenteritis was important in the development of IBS, in two acute rodent infection studies, intestinal injury was only marginally altered by the presence or absence of intact CdtB. Thus, Cdt B appeared to have another role in vivo towards the development of IBS.

We demonstrate herein, using an immunohistochemical approach, that CdtB is producing an effect on the host through the production of autoantibodies. Antibodies to CdtB bind to the myenteric neurons and the interstitial cells of Cajal. These autoantibodies are detectable in both rats and humans with post-infectious IBS. In fact, the antibody has a significant diagnostic value in both identifying post-infectious IBS (even in contrast to Crohns and ulcerative colitis) and in predicting the consequence of a small bowel neuropathy (small intestinal bacterial overgrowth) in rats. These data suggest that IBS is an autoimmune disease.

Based on the current evidence, it now seems that post-infectious IBS could account for a majority of IBS in the US population and recent evidence supports that SIBO is common in IBS (Posserud and Pyleris) and may be due to neuromuscular disturbance of the small intestine. However, this study suggests a sequence of events leading to this disturbance that starts with exposure to a bacterial pathogen containing CdtB. The resulting immune response to CdtB produces antibodies that also recognize a host enteric nerve cytosolic protein. The resulting autoantibody and its titer appear to correlate with the degree of SIBO which might be an indirect measure of the neuronal impairment of the small bowel. The degree and presence of SIBO appears to determine the bowel disturbance in this model (the first rat model validation) and in humans (Target 1 and 2) studies.

In conclusion, while not wishing to be bound by any particular theory, we believe that acute gastroenteritis is a major cause of IBS. Herein, we demonstrate that the cytolethal distending toxin is instrumental in the development of IBS through the induction of an antibody and through molecular mimicry one that is autoimmune to an enteric nerve protein and predictive of SIBO. This study may be a major breakthrough in understanding the pathophysiology of IBS.

Accordingly, various embodiments of the present invention are based, at least in part, on these findings.

Diagnosis

Various embodiments provide for a method and a system of diagnosing a gastrointestinal motility disorder, bladder motility disorder, or fibromyalgia.

In various embodiments, the method comprises: providing a biological sample from a subject desiring diagnosis of the gastrointestinal motility disorder, bladder motility disorder, or fibromyalgia, detecting in the biological sample, a presence of anti-vinculin antibodies, and determining a presence or likely presence of the gastrointestinal motility disorder, bladder motility disorder, or fibromyalgia if the presence of anti-vinculin antibodies are detected, or determining an absence or likely absence of the gastrointestinal motility disorder, bladder motility disorder, or fibromyalgia if the absence of anti-vinculin antibodies are detected. In certain embodiments, the method further comprises analyzing the biological sample for the presence or absence of anti-vinculin antibodies.

In various embodiments, the method comprises: providing a biological sample from a subject desiring diagnosis of the gastrointestinal motility disorder, bladder motility disorder, or fibromyalgia, detecting in the biological sample, a level of anti-vinculin antibodies, and determining a presence or likely presence of the gastrointestinal motility disorder, bladder motility disorder, or fibromyalgia if the level of an anti-vinculin antibody is higher than an established control level, or determining the absence or likely absence of the gastrointestinal motility disorder, bladder motility disorder, or fibromyalgia if the level of an anti-vinculin antibody is equal or lower than the established control level. In various embodiments, the established control level is a level of anti-vinculin antibodies within two standard deviations of anti-vinculin antibody levels from subjects without the gastrointestinal motility disorder, bladder motility disorder, or fibromyalgia. In certain embodiments, the method further comprises analyzing the biological sample for a level of anti-vinculin antibodies.

In various embodiments, the method comprises: providing a biological sample from a subject desiring diagnosis of the gastrointestinal motility disorder, bladder motility disorder, or fibromyalgia, detecting in the biological sample, a level of anti-vinculin antibodies, and determining a presence or likely presence of the gastrointestinal motility disorder, bladder motility disorder, or fibromyalgia if the level of anti-vinculin antibodies is significantly higher than an established control level, or determining the absence or likely absence of the gastrointestinal motility disorder, bladder motility disorder, or fibromyalgia if the level of anti-vinculin antibodies is not significantly higher than the established control level. In various embodiments the established control level is a level of anti-vinculin antibodies from subjects without the gastrointestinal motility disorder, bladder motility disorder, or fibromyalgia. In certain embodiments, the method further comprises analyzing the biological sample for a level of anti-vinculin antibodies.

In various embodiments, the system comprises: an isolated biological sample from a subject desiring diagnosis of the gastrointestinal motility disorder, bladder motility disorder, or fibromyalgia, and an assay for detecting in the biological sample, a presence or level of an anti-vinculin antibody.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample, a second reagent (e.g., secondary antibody) to react with the anti-vinculin antibody, and a substrate. In various embodiments, the first reagent is vinculin or a fragment thereof, which will react with the anti-vinculin antibody if present in the biological sample. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of the gastrointestinal motility disorder, bladder motility disorder, or fibromyalgia if the presence of anti-vinculin antibodies is detected, or determining an absence or likely absence of the gastrointestinal motility disorder, bladder motility disorder, or fibromyalgia if the absence of anti-vinculin antibodies is detected. In various embodiments, the machine is a computer. In various embodiments, the computer comprises a display element for displaying whether there is a presence or absence of the gastrointestinal motility disorder, bladder motility disorder, or fibromyalgia.

In various embodiments, the system further comprises a machine for determining a presence or likely presence of the gastrointestinal motility disorder, bladder motility disorder, or fibromyalgia if the level of anti-vinculin antibodies is higher than an established control level, or determining an absence or likely absence of the gastrointestinal motility disorder, bladder motility disorder, or fibromyalgia if the level of anti-vinculin antibodies is equal or lower than the established control level. In various embodiments, the established control level is a level of anti-vinculin antibodies within two standard deviations of anti-vinculin antibody levels from subjects without the gastrointestinal motility disorder, bladder motility disorder, or fibromyalgia. In certain embodiments, the method further comprises analyzing the biological sample for a level of anti-vinculin antibodies.

In various embodiments, the system further comprises a machine for determining a presence or likely presence of the gastrointestinal motility disorder, bladder motility disorder, or fibromyalgia if the level of anti-vinculin antibodies is significantly higher than an established control level, or determining an absence or likely absence of the gastrointestinal motility disorder, bladder motility disorder, or fibromyalgia if the level of anti-vinculin antibodies is not significantly higher than the established control level. In various embodiments the established control level is a level of anti-vinculin antibodies from subjects without the gastrointestinal motility disorder, bladder motility disorder, or fibromyalgia. In certain embodiments, the method further comprises analyzing the biological sample for a level of anti-vinculin antibodies.

In various embodiments, the gastrointestinal motility disorder, bladder motility disorder, or fibromyalgia detected by the method or system is irritable bowel syndrome (IBS), constipation predominant IBS (C-IBS), diarrhea predominant IBS (D-IBS), alternating IBS (A-IBS) (more recently re-named as mixed (M-IBS)), gastroesophageal reflux disease (GERD), functional dyspepsia, post-infectious irritable bowel syndrome (PI-IBS), small intestinal bacterial overgrowth (SIBO), gastroesophageal reflux disease (GERD), gastroparesis, allergic/eosinophilic gastroenteritis, constipation, chronic constipation, pseudo-obstruction, insterstitial cystitis, leaky gut syndrome, or fibromyalgia. Without being bound to any particular theory, we believe that since vinculin helps cells migrate and adhere to each other and epithelial cells have vinculin, impaired vinculin may allow the gut to be "leaky." In the case of the enteric nervous system, impaired vinculin may impair the enteric nerve network. In various embodiments, the gastrointestinal motility disorder is IBS. In various embodiments, the gastrointestinal motility disorder is GERD. In various embodiments, the gastrointestinal motility disorder is functional dyspepsia.

In certain embodiments, the subject desiring diagnosis of the gastrointestinal motility disorder, bladder motility disorder, or fibromyalgia in accordance to the methods and systems of the present invention may have one or more symptoms indicative of the gastrointestinal motility disorder, bladder motility disorder, or fibromyalgia; for example, bloating, diarrhea, constipation, abdominal pain, fatigue, fibromyalgia pain.

Various embodiments of the present invention provide for a method and a system of distinguishing between IBS and IBD.

The method can comprise providing a biological sample from a subject desiring a diagnosis to distinguish between IBS and IBD, detecting in the biological sample, a presence of anti-vinculin antibodies, and making a diagnosis of IBS if the presence of anti-vinculin antibodies is detected, or making a diagnosis of IBD if the absence of anti-vinculin antibodies is detected. In certain embodiments, the method further comprises analyzing the biological sample for the presence or absence of anti-vinculin antibodies. In certain embodiments, the method further comprises selecting an IBS treatment if IBS is diagnosed, or selecting an IBD treatment if IBD is diagnosed.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is higher than an established control level, or making a diagnosis of IBD if the level of anti-vinculin antibodies is equal or lower than the established control level. In various embodiments, the established control level is a level of anti-vinculin antibodies within two standard deviations of anti-vinculin antibody levels from healthy subjects without IBS, IBD or both. In certain embodiments, the method further comprises analyzing the biological sample for a level of anti-vinculin antibodies.

In various embodiments, the method can comprise providing a biological sample from a subject desiring a diagnosis to distinguish between IBS and IBD, detecting in the biological sample, a level of anti-vinculin antibodies, and making a diagnosis of IBS if the level of anti-vinculin antibodies is significantly higher than an established control level, or making a diagnosis of IBD if the level of anti-vinculin antibodies is not significantly higher than the established control level. In various embodiments the established control level is a level of anti-vinculin antibodies from subjects without IBS, IBD or both. In certain embodiments, the method further comprises analyzing the biological sample for a level of anti-vinculin antibodies.

In various embodiments, the system can comprise an isolated biological sample from a subject desiring distinguishing between IBS and IBD, and an assay for detecting in the biological sample, a presence of an anti-vinculin antibody or a level of anti-vinculin antibody to distinguish between IBS and IBD.

In various embodiments the assay is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence or likely presence of IBS if the presence of anti-vinculin antibodies is detected, or determining the presence or likely presence of IBD if the absence of anti-vinculin antibodies is detected. In various embodiments, the machine is a computer. In various embodiments, the computer comprises a display element for displaying whether the patient likely has IBS or IBD.

In various embodiments, the system further comprises a machine for determining a presence or likely presence of IBS if the level of anti-vinculin antibodies is higher than an established control level, or determining a presence or likely presence of IBD if the level of anti-vinculin antibodies is equal or lower than the established control level. In various embodiments, the established control level is a level of anti-vinculin antibodies within two standard deviations of anti-vinculin antibody levels from healthy subjects without IBS, IBD or both. In certain embodiments, the method further comprises analyzing the biological sample for a level of anti-vinculin antibodies.

In various embodiments, the system further comprises a machine for determining a presence or likely presence of IBS if the level of anti-vinculin antibodies is significantly higher than an established control level, or determining a presence or likely presence of IBD if the level of anti-vinculin antibodies is not significantly higher than the established control level. In various embodiments the established control level is a level of anti-vinculin antibodies from healthy subjects without IBS, IBD or both. In certain embodiments, the method further comprises analyzing the biological sample for a level of anti-vinculin antibodies.

In various embodiments, the machine is a computer. In various embodiments, the computer comprises a display element for displaying whether the patient likely has IBS or IBD.

In various embodiments, the anti-vinculin antibody detected in these methods or systems is an antibody that binds specifically to vinculin.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 contiguous residues of vinculin.

In various embodiments, the anti-vinculin antibody is an antibody that binds specifically to SEQ ID NO:1.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:1.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:1.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 contiguous residues of SEQ ID NO:1.

Contiguous residues of vinculin or SEQ ID NO:1 include those beginning at any amino acid and ending at any amino acid of vinculin or SEQ ID NO:1.

```
Protein sequence of Vinculin (SEQ ID NO: 1):
MPVFHTRTIESILEPVAQQISHLVIMHEEGEVDGKAIPDLTAPVAAVQAA

VSNLVRVGKETVQTTEDQILKRDMPPAFIKVENACTKLVQAAQMLQSDPY

SVPARDYLIDGSRGILSGTSDLLLTFDEAEVRKIIRVCKGILEYLTVAEV

VETMEDLVTYTKNLGPGMTKMAKMIDERQQELTHQEHRVMLVNSMNTVKE

LLPVLISAMKIFVTTKNSKNQGIEEALKNRNFTVEKMSAEINEIIRVLQL

TSWDEDAWASKDTEAMKRALASIDSKLNQAKGWLRDPSASPGDAGEQAIR

QILDEAGKVGELCAGKERREILGTCKMLGQMTDQVADLRARGQGSSPVAM

QKAQQVSQGLDVLTAKVENAARKLEAMTNSKQSIAKKIDAAQNWLADPNG

-continued
GPEGEEQIRGALAEARKIAELCDDPKERDDILRSLGEISALTSKLADLRR

QGKGDSPEARALAKQVATALQNLQTKTNRAVANSRPAKAAVHLEGKIEQA

QRWIDNPTVDDRGVGQAAIRGLVAEGHRLANVMMGPYRQDLLAKCDRVDQ

LTAQLADLAARGEGESPQARALASQLQDSLKDLKARMQEAMTQEVSDVFS

DTTTPIKLLAVAATAPPDAPNREEVFDERAANFENHSGKLGATAEKAAAV

GTANKSTVEGIQASVKTARELTPQVVSAARILLRNPGNQAAYEHFETMKN

QWIDNVEKMTGLVDEAIDTKSLLDASEEAIKKDLDKCKVAMANIQPQMLV

AGATSIARRANRILLVAKREVENSEDPKFREAVKAASDELSKTISPMVMD

AKAVAGNISDPGLQKSFLDSGYRILGAVAKVREAFQPQEPDFPPPPPDLE

QLRLTDELAPPKPPLPEGEVPPPRPPPPEEKDEEFPEQKAGEVINQPMMM

AARQLHDEARKWSSKGNDIIAAAKRMALLMAEMSRLVRGGSGTKRALIQC

AKDIAKASDEVTRLAKEVAKQCTDKRIRTNLLQVCERIPTISTQLKILST

VKATMLGRTNISDEESEQATEMLVHNAQNLMQSVKETVREAEAASIKIRT

DAGFTLRWVRKTPWYQ
```

In various embodiments, detecting the presence or absence of the antibody is performed on a biological sample obtained from the subject. In another embodiment, detecting the presence or absence of the antibody is performed on a blood, serum, or stool sample obtained from the subject. One of ordinary skill in the art will readily appreciate methods and systems that can be used to detect the presence or absence of an antibody that binds specifically to vinculin, SEQ ID NO: 1 or a fragment thereof. These methods and systems include but are not limited to ELISA, immunohistochemistry, flow cytometry, fluorescence in situ hybridization (FISH), radioimmuno assays, and affinity purification.

In various embodiments, vinculin, SEQ ID NO: 1 or a fragment thereof (as described above) is used as a substrate or reagent (e.g., collector, trap) to bind anti-vinculin antibodies (if present).

In certain embodiments, detecting the presence or absence of an antibody that binds specifically to vinculin, SEQ ID NO: 1 or a fragment thereof may be performed by contacting vinculin, SEQ ID NO: 1 or a fragment thereof to a biological sample obtained from the subject to isolate the antibody that binds specifically to vinculin, SEQ ID NO: 1 or a fragment thereof, wherein the isolation of the antibody that binds specifically to vinculin, SEQ ID NO: 1 or a fragment thereof indicates the presence of the antibody and the lack of isolation of the antibody that binds specifically to vinculin, SEQ ID NO: 1 or a fragment thereof indicates the lack of the antibody. In various embodiments, the fragment of vinculin or SEQ ID NO: 1 may be the fragments as described herein. As an example, an affinity matrix comprising vinculin, SEQ ID NO: 1 or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on vinculin, SEQ ID NO: 1 or a fragment thereof; the labeled vinculin, SEQ ID NO: 1 or a fragment thereof can be contacted with a biological sample to allow the antibody (if present) to bind specifically to the labeled vinculin, SEQ ID NO: 1 or a fragment thereof. In various embodiments, the labeled vinculin, SEQ ID NO: 1 or a fragment thereof can be separated out and analyzed for its binding to the antibody.

Therapy

Various embodiments provide for a method of selecting a therapy for a gastrointestinal motility disorder, bladder motility disorder, or fibromyalgia for a subject in need thereof. In various embodiments, the method comprises: detecting the presence of anti-vinculin antibodies; and selecting a therapy to treat the gastrointestinal motility disorder, bladder motility disorder, or fibromyalgia. Selecting a therapy as used herein, includes but is not limited to selecting, choosing, prescribing, advising, recommending, instructing, or counseling the subject with respect to the treatment. In various embodiments, the method further comprises administering the therapy to treat the gastrointestinal motility disorder, bladder motility disorder, or fibromyalgia. In various embodiments, the therapy is a therapy as described herein. In various embodiments, the available therapy comprises administering a course of antibiotic therapy to treat the gastrointestinal motility disorder, bladder motility disorder, or fibromyalgia. In various embodiments, the therapy is an available therapy in the prior art.

In various embodiments, detecting the presence of anti-vinculin antibodies can be performed as described by the methods or systems of the present invention.

In various embodiments, the subject can be a subject presenting one or more symptoms of gastrointestinal motility disorder, bladder motility disorder, or fibromyalgia; for example, as discussed herein.

In various embodiments, the method comprises: detecting the presence of anti-vinculin antibodies; and selecting a course of antibiotic therapy to treat gastrointestinal motility disorder, bladder motility disorder, or fibromyalgia. In various embodiments, the method further comprises administering the course of antibiotic therapy treat the gastrointestinal motility disorder, bladder motility disorder, or fibromyalgia.

In various embodiments, the gastrointestinal motility disorder, bladder motility disorder, or fibromyalgia can be part of irritable bowel syndrome (IBS), C-IBS, D-IBS, A-IBS (also known as M-IBS), gastroesophageal reflux disease (GERD), functional dyspepsia, post-infectious irritable bowel syndrome (PI-IBS), small intestinal bacterial overgrowth (SIBO), gastroesophageal reflux disease (GERD), gastroparesis, allergic/eosinophilic gastroenteritis, constipation, chronic constipation, pseudo-obstruction, insterstitial cystitis, leaky gut syndrome, or fibromyalgia. In various embodiments, the gastrointestinal motility disorder is IBS. In certain embodiments, the gastrointestinal motility disorder is GERD. In certain embodiments, the gastrointestinal motility disorder is functional dyspepsia.

Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. In various embodiments, the antibiotics are a combination of rifaximin and neomycin. In various embodiments, the antibiotics are a combination of rifaximin and doxycycline. In various embodiments, the antibiotics are a combination of rifaximin and metronidazole.

In various embodiments, the antibiotics are non-absorbable antibiotics. Examples of non-absorbable antibiotics include but are not limited to rifaximin, neomycin, Bacitracin, vancomycin, teicoplanin, ramoplanin, and paromomycin.

Various embodiments provide for methods for treating a gastrointestinal motility disorder, bladder motility disorder, or fibromyalgia. In various embodiments, the gastrointestinal motility disorder, bladder motility disorder, or fibromyalgia treated can be irritable bowel syndrome (IBS), C-IBS, D-IBS, A-IBS (also known as M-IBS), gastroesophageal reflux disease (GERD), functional dyspepsia, post-infectious irritable bowel syndrome (PI-IBS), small intestinal bacterial overgrowth (SIBO), gastroesophageal reflux disease (GERD), gastroparesis, allergic/eosinophilic gastroenteritis, constipation, chronic constipation, pseudo-obstruction, insterstitial cystitis, leaky gut syndrome, or fibromyalgia. In various embodiments, the gastrointestinal motility disorder is IBS. In certain embodiments, the gastrointestinal motility disorder is GERD. In certain embodiments, the gastrointestinal motility disorder is functional dyspepsia.

In various embodiments, the method can comprise providing an anti-vinculin antibody neutralizing or inhibiting agent and administering the anti-vinculin antibody neutralizing or inhibiting agent to a subject in need thereof to neutralize or inhibit the anti-vinculin antibody.

In various embodiments, the anti-vinculin antibody neutralizing or inhibiting agent is a polypeptide capable of binding to the anti-vinculin antibody and neutralizing or inhibiting its function.

In various embodiments, the anti-vinculin antibody neutralizing or inhibiting agent is a polypeptide capable of binding to an antigen binding site of the anti-vinculin antibody. While not wishing to be bound by any particular theory, the inventors believe that these polypeptides can serves as a decoy to the anti-vinculin antibody. In various embodiments, the polypeptides are CDT pentapeptides as disclosed by Lucchese and Delfino (*Developing an anti-Campylobacter jejuni vaccine*. Immunopharmacology and Immunotoxicology, 2012; Early Online: 1-6), which is hereby incorporated by reference in its entirety as though fully set forth.

In various embodiments, the anti-vinculin antibody neutralizing or inhibiting agent is a small molecule capable of binding to the anti-vinculin antibody and neutralizing or inhibiting its function.

In various embodiments, the anti-vinculin antibody neutralizing or inhibiting agent is a small molecule capable of binding to an antigen binding site of the anti-vinculin antibody.

In various embodiments, the method can comprise providing an agent to change vinculin from an inactive state to an active state; and administering the agent to a subject in need thereof to treat the gastrointestinal motility disorder, bladder motility disorder, or fibromyalgia.

In various embodiments, the agent to change vinculin from an inactive state to an active state is a small molecule capable of activating vinculin.

In various embodiments, the method can comprise providing a vinculin agonist; and administering the vinculin agonist to a subject in need thereof to treat the gastrointestinal motility disorder, bladder motility disorder, or fibromyalgia. In certain embodiments, the vinculin agonist can be vinculin activating peptide (VAP) as disclosed by Nelson et al., *Vinculin Activators Target Integrins from Within the Cell to Increase Melanoma Sensitivity to Chemotherapy*, MOL CANCER RES JUNE 2011 9; 712 (published online Apr. 1, 2011), which is hereby incorporated by reference in its entirety as though fully set forth. In various embodiments, the VAP can be residues 500-633 of invasin protein IpaA of *Shigella*.

The protein sequence of IpaA of *Shigella*:

```
                                          (SEQ ID NO: 6)
MHNVNNTQAP TFLYKATSPS STEYSELKSK ISDIHSSQTS

LKTPASVSEK ENFATSFNQK CLDFLFSSSG KEDVLRSIYS

NSMNAYAKSE ILEFSNVLYS LVHQNGLNFE NEKGLQKIVA

QYSELIIKDK LSQDSAFGPW SAKNKKLHQL RQNIEHRLAL

LAQQHTSGEA LSLGQKLLNT EVSSFIKNNI LAELKLSNET

VSSLKLDDLV DAQAKLAFDS LRNQRKNTID SKGFGIGKLS

RDLNTVAVFP ELLRKVLNDI LEDIKDSHPI QDGLPTPPED

MPDGGPTPGA NEKTSQPVIH YHINNDNRTY DNRVFDNRVY

DNSYHENPEN DAQSPTSQTN DLLSRNGNSL LNPQRALVQK

VTSVLPHSIS DTVQTFANNS ALEKVFNHTP DNSDGIGSDL

LTTSSQERSA NNSLSRGHRP LNIQNSSTTP PLHPEGVTSS

NDNSSDTTKS SASLSHRVAS QINKFNSNTD SKVLQTDFLS

RNGDTYLTRE TIFEASKKVT NSLSNLISLI GTKSGTQERE

LQEKSKDITK STTEHRINNK LKVTDANIRN YVTETNADTI

DKNHAIYEKA KEVSSALSKV LSKIDDTSAE LLTDDISDLK

NNNDITAENN NIYKAAKDVT TSLSKVLKNI NKD
```

In various embodiments, the method can comprise providing a vinculin activator; and administering the vinculin activator to a subject in need thereof to treat the gastrointestinal motility disorder, bladder motility disorder, or fibromyalgia. In certain embodiments, the vinculin activator can be talin, f-actin, a-catenin, or combinations thereof.

Various embodiments provide for a method of treating or inhibiting the progression of colon polyps or malignancy. It has been seen that there are less polyps in patients with IBS. As such, anti-vinculin antibodies or agents that block vinculin can decrease the progression of colon polyps or malignancy.

In various embodiments, the method can comprise providing an agent to change vinculin from an active state to an inactive state; and administering the agent to a subject in need thereof to treat or inhibit the progression of colon polyps or malignancy.

In various embodiments, the agent to change vinculin from an active state to an inactive state is a small molecule capable of inactivating vinculin.

In various embodiments, the method can comprise providing a vinculin antagonist; and administering the vinculin antagonist to a subject in need thereof to treat or inhibit the progression of colon polyps or malignancy.

In various embodiments, the method can comprise providing a vinculin inactivator; and administering the vinculin inactivator to a subject in need thereof to treat or inhibit the progression of colon polyps or malignancy.

In various embodiments, the method can comprise providing an anti-vinculin antibody capable of inhibiting the function of vinculin; and administering the anti-vinculin antibody to the subject to treat or inhibit the progression of colon polyps or malignancy.

In various embodiments, the present invention provides pharmaceutical compositions including a pharmaceutically acceptable excipient along with a therapeutically effective amount of the agents described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Methods

Healthy control subjects, IBS subjects and subjects with inflammatory bowel disease (IBD) were recruited and serum was collected. The ELISA was prepared by coating 96 well plates with recombinant cdtB and human vinculin. After coating, a calibration curve was made for cdtB and vinculin using purified commercial anti-cdtB and anti-human-vinculin. Serum from healthy controls, IBS and IBD subjects was added to the wells and examined. The wells were incubated for 60 minutes prior to washing and application of secondary antibodies.

Example 2

Anti-CdtB Antibodies

To determine the role of CdtB in the development of IBS, two antibodies were developed to CdtB from *C. jejuni* 81-176. The first was through immunization of rabbits with an 18 amino acid residue identified as highly antigenic (haAB) through protein modeling (AnaSpec, San Jose, Calif.). The second was developed through immunization of rabbits with the near full length CdtB peptide (wAb). To confirm the selectivity of rabbit serum to CdtB, lysates of *C. jejuni* 81-176, were run on western gel with and without blocking with CdtB protein to verify a 28 kDa band. With this validation, the wAb was used through the remaining experiments.

Example 3

Acute *C. jejuni* Exposure and CdtB in Rats Acutely Infected with *C. jejuni*

To determine the role of CdtB in our animal model, we examined ileal tissue in rats acutely infected with *C. jejuni*. Rats were gavaged with $10^8$ cfu/mL of *C. jejuni* 81-176. On day 2, rats were euthanized and sections of ileum were resected, fixed in 10% formalin (VWR, Radnor, Pa.), and sections prepared for immunohistochemistry. As a comparison, ileum from rats naïve to *C. jejuni* were similarly prepared. To these sections wAb and preimmune rabbit serum (negative control) were applied to contiguous sections.

Example 4

Anti-CdtB Antibody Tracking in Human Ileum

Based on finding activity of wAb to mucosa and neural elements of both *C. jejuni* infected and control rats, the study was repeated using human ileum sections. Humans who underwent ileocecectomy for colon malignancy were identified and a portion of the ileum was mounted and sections were incubated with wAb and preimmune serum using immunohistochemistry to determine if there was support for molecular mimicry.

Example 5

Identification of Enteric Neuronal Protein Responsible for Molecular Mimicry Since the enteric nervous system and in particular ganglia and enteric neuron was a site of localization for antibodies to CdtB (wAb), enteric neuronal stem cell lysates were obtained. Lysates were run on western gel with and without blocking with CdtB protein using wAb and haAB to identify a potential protein to which wAb was adhering. This was identified at 117 kDa and subsequently immunoprecipitation using wAb applied to beads was used to draw down the protein of interest. This was done by binding—proteins to beads then binding from lysates of $2.5\times10^8$ enteric neuronal stem cells through. Effluent was run on a gel and the band again identifying a protein at 117 kDa. This band was cut and mass spectroscopy was used to analyze the protein content.

After the identification of the protein of interest, confocal microscopy was used to determine the co-localization of antibodies to this protein in the tissue in comparison to tissue affinity with CdtB wAb in both rats and humans.

Example 6

Detection of Antibodies to CdtB and Vinculin in Rats Exposed to C. jejuni

In our validated animal model of post-infectious IBS, male Sprague-Dawley rats exposed to C. jejuni 81-176 develop small intestinal bacterial overgrowth based on total bacterial counts by qPCR. This phenotype is augmented by repeated exposure to C. jejuni. In this experiment, 3 groups of rats are compared. The first group includes control rats that have never been exposed to C. jejuni (n=20). In the second group of rats, the animals were gavaged with vehicle as juveniles and 2 months later received a gavage of $10^8$ cfu/mL of C. jejuni 81-176 as adults (J−/A+) (n=50). The third group of animals were gavaged with $10^8$ cfu/mL of C. jejuni 81-176 as juveniles and re-expose by gavage with $10^8$ cfu/mL of C. jejuni 81-176 two months later as adults (J+/A+) (n=50). After the adult exposure, C. jejuni clearance from stool culture was achieved by 30 days. Rats were then euthanized 90 days after clearance of C. jejuni to guarantee they were truly post-infectious as previously reported. During dissection, sections of duodenum, jejunum and ileum were formalin fixed and resected for histology and luminal bacterial quantitation was done by qPCR as previous reported. At time of euthanasia, intra-cardiac puncture was used to collect blood and serum was separated and stored.

Example 7

ELISA Methodology

Antigens (whole CdtB or vinculin (Novo, Short Hills, N.J.)) were bound to 96 well plates under humidified conditions overnight at 4° C. using 100 μl/well 0.125 μg/ml protein in BBS (Pierce). Wells were washed with 0.05% PBS-T and blocked with 120 μl/well of 0.5% BSA/PBS for 1 hour at room temperature in the humidified box. Samples (rat serum, human serum) as well as controls: wAB, vinculin Ab (Santa Cruz, Santa Cruz, Calif.) were added at a 1:100 dilution in 0.5% BSA/PBS for 2 hrs at room temperature in humidified box. Secondary antibody, human, rat or goat IgG conjugated with HRP (Jackson ImmunoResearch, West Grove, Pa.) was added 100 μl/well, 1:1000 dilution in 0.5% BSA/PBS for 30 min at room temperature in humidified box. The plates were washed with 0.05% PBS-T before adding 100 μl/well of substrate solution (Jackson ImmunoResearch, West Grove, Pa.) and read in plate reader after application of rat or human serum as indicated below (BioTek Synergy HT)

Example 8

ELISA in Rats with and without Campylobacter Infection and Overgrowth

Serum from each of the 3 groups of rats was assayed: uninfected, single campylobacter exposure as adult, and immature and adult double infected. The resulting OD was compared between the 3 groups as well as rats segregated with and without small intestinal bacterial overgrowth (defined as >2 SD above the mean) as previously published. Finally, a correlation curve was created comparing the level of serum antibody to the degree of bacteria in the ileum.

Example 9

ELISA in Humans with IBS

Three groups of humans were used to evaluate the titer of anti-CdtB and anti-vinculin antibodies. The first group was a group of healthy controls. Healthy control subjects were defined as subjects, who on questionnaire, reported no altered bowel function, no bloating and no abdominal pain (each less than 10 mm on a 100 mm VAS scale for the specific symptom). The second group was a group of diarrhea predominant IBS subjects based on Rome III criteria. The third group was composed of 10 subjects with Crohn's disease and 10 subjects with ulcerative colitis. ELISA was set up similar to the rat study. Titers of anti-CdtB and anti-vinculin were compared between the 3 groups. In addition, correlation was conducted between anti-CdtB and anti-vinculin. Finally, two unrelated proteins, c-kit and latrophillin were used in ELISA to determine control for nonspecific binding in humans with IBS.

Example 10

Immunofluorescence, Confocal Imaging of Anti-cdtB Antibody, Neural Markers and Vinculin Since there was evidence of neuronal binding by wAb, particularly the perigangliar regions and the deep muscular plexus interstitial cells of Cajal (DMP-ICC) in immunohistochemistry, colocalization experiments were undertaken comparing localization of wAb to anti-c-kit (R&D Systems, Minneapolis, Minn.), S-100 (neuronal) (Pierce Biotechnology, Rockford, Ill.) and PGP 9.5 (ganglia) (Pierce Biotechnology, Rockford, Ill.) and anti-vinculin (Santa Cruz, Santa Cruz, Calif.) all raised in goat. Confocal microscopic images were taken of contiguous sections of ileum from rats and humans for comparison.

Briefly, slides of acutely C. Jejuni infected and uninfected rat ileum and were deparaffinized and washed in sequentially in xylenes and ethanol before antigen retrieval and serum blocking Primary antibodies were added (1:200 wAb raised in rabbit plus 1:100 c-kit, S100, PGP 9.5, or vinculin antibodies raised in goat) and incubated at room temperature in humidified conditions. Slides treated with primary antibody were washed in PBS and incubated with 1:30 DAPI (Invitrogen, Grand Island, N.Y.) and secondary antibodies: Alexa red 568 anti-goat (Invitrogen, Grand Island, N.Y.) for c-kit, S100, PGP 9.5 or vinculin antibodies (1:300) and Alexa green 488 anti-rabbit (Invitrogen, Grand Island, N.Y.) for wAB (1:300). After incubation in dark, humidified conditions, Prolong Gold (Invitrogen, Grand Island, N.Y.) was added and section covered with glass for viewing under Confocal Microscopy (Leica TCS SP5× microscope, Leica SCN400 F digital slide scanner.)

Example 11

Gene Expression of Vinculin in Rats with and without SIBO

Rat ileal tissue RNA was extracted (Qiagen) from 3 months post *C. jejuni* infected and control uninfected animals and converted to cDNA by iScript reverse transcription (Bio Rad, Hercules, Calif.). Quantitative PCR was performed with primers specific to rat vinculin and normalized to gene expression of beta actin.

| | Primers | |
|---|---|---|
| beta actin[1] | FW: GGAGATTACTGCCCTGGCTCCTA (SEQ ID NO: 2) REV: GACTCATCGTACTCCTGCTTGCTG (SEQ ID NO: 3) | Amp: 150 bp |
| Vinculin[2] | FW: GCCAAGCAGTGCACAGATAA (SEQ ID NO: 4) REV: TCTTTCTAACCCAGCGCAGT (SEQ ID NO: 5) | Amp: 273 bp |

[1]Reference: Qian-Qian Liang et al., (2010) Herb Formula "Fufangqishe-Pill" Prevents Upright Posture-Induced Intervertebral Disc Degeneration at the Lumbar in Rats. J Pharmacol Sci 113: 23-31)
[2]Reference: Zhang et al., Proteome Science 2010 8:12 (doi: 10.1186/1477-5956-8-12)

Example 12

Statistical Analysis

The comparison of anti-CdtB and anti-vinculin levels between groups was compared by the non-parametric Mann-Whitney U test. Correlation curves between bacteria counts and antibody titers were compared by Pearson correlation. Pearson correlation was also used to compared anti-CdtB and anti-vinculin in humans. In the determination of a positive and negative ELISA a Chi-square was performed. For the comparison of ELISA to the colony counts of small bowel flora, a Pearson rank correlation was used. Finally, thresholds for anti-CdtB (>2.0 OD) and anti-vinculin (>1.2 OD) as a method of diagnosing IBS compared to controls and subjects with inflammatory bowel disease. Test characteristics such as sensitivity and specificity were determined based on these thresholds. Differences between groups was determined to be significant if P<0.05 and data are expressed as mean±SD.

Example 13

Results 19 healthy controls, 20 IBD subjects and 42 IBS subjects participated in the study. Demographics were similar between groups. For the detection of anti-cdtB, an Optical density of ≥2.0 was set as positive and for the detection of anti-human vinculin antibodies an OD was set at ≥1.2. Based on these cutoffs, using either anti-vinculin or anti-cdtB was successful in diagnosing IBS over IBD or health controls (Table 1a). Since anti-cdtB is anti-vinculin, it would be expected that titers of serum anti-cdtB in all subjects would correspond to anti-human vinculin and this was found to be true (R=0.58, P<0.001).

TABLE 1a

| | IBS vs all others | | IBS vs Health | | IBS vs IBD | |
|---|---|---|---|---|---|---|
| | Sensitivity | Specificity | Sensitivity | Specificity | Sensitivity | Specificity |
| Anti-vinculin | 58.6 | 94.1 | 58.6 | 87.5 | 58.6 | 100 |

Example 14

Validation of Anti-CdtB Antibodies

In order to validate the anti-CdtB antibodies, western blots were prepared with purified CdtB. Using both antibodies generated to whole CdtB (wAB) (FIG. 1a) and antibody to the highly antigenic 18 residue sequence of CdtB (haAb) (FIG. 1b) both recognized the CdtB as an active band at 27 kDa (the molecular weight of CdtB). Rabbit preimmune serum did not recognize CdtB and blocking the haAb with the peptide resulted in no visible band (FIG. 1c).

Figure 2:
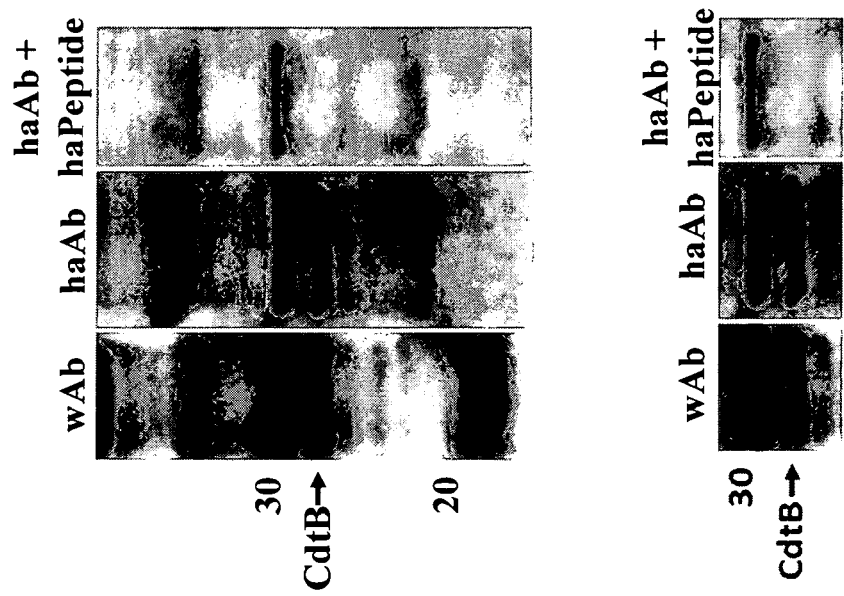
FIG. 2 depicts Western blot of C. lysates vs. antibody in accordance with various embodiments of the present invention.

To validate that the antibody recognized CdtB in *C. jejuni*, another western blot was prepared and run with a lysate of *C. jejuni* 81-176. This demonstrated that wAb (FIG. 2a) and haAb (FIG. 2b) recognized the CdtB as an active band at 27 kDa (the molecular weight of CdtB). Blocking the haAb with peptide eliminated detection of a band at 27 kDa (FIG. 2c).

Example 15 wAb in Rats Exposed and Unexposed to *C. jejuni*

Figure 3:
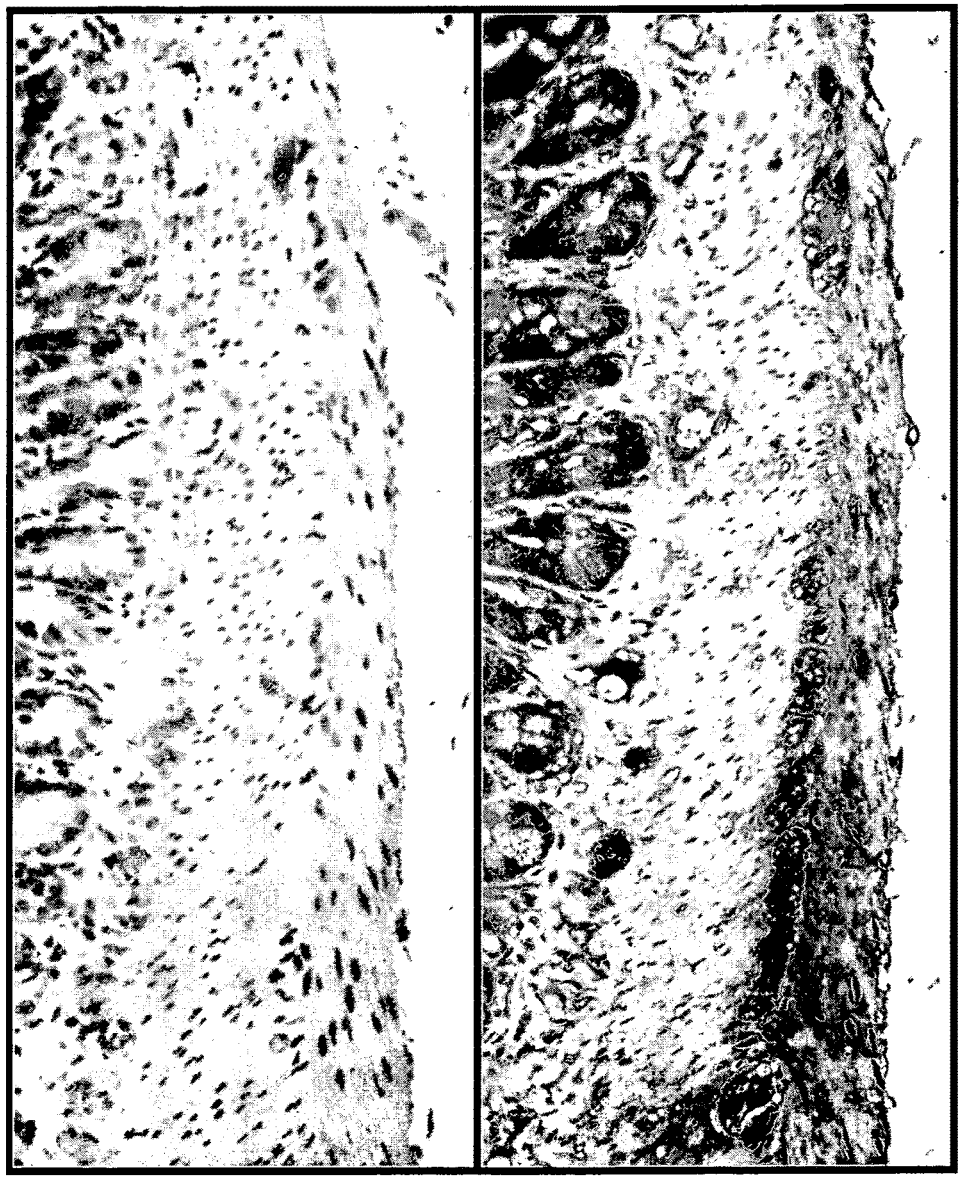
FIG. 3 depicts immunohistochemistry of samples from acute rats, day 2 in accordance with various embodiments of the present invention.
Figure 4:
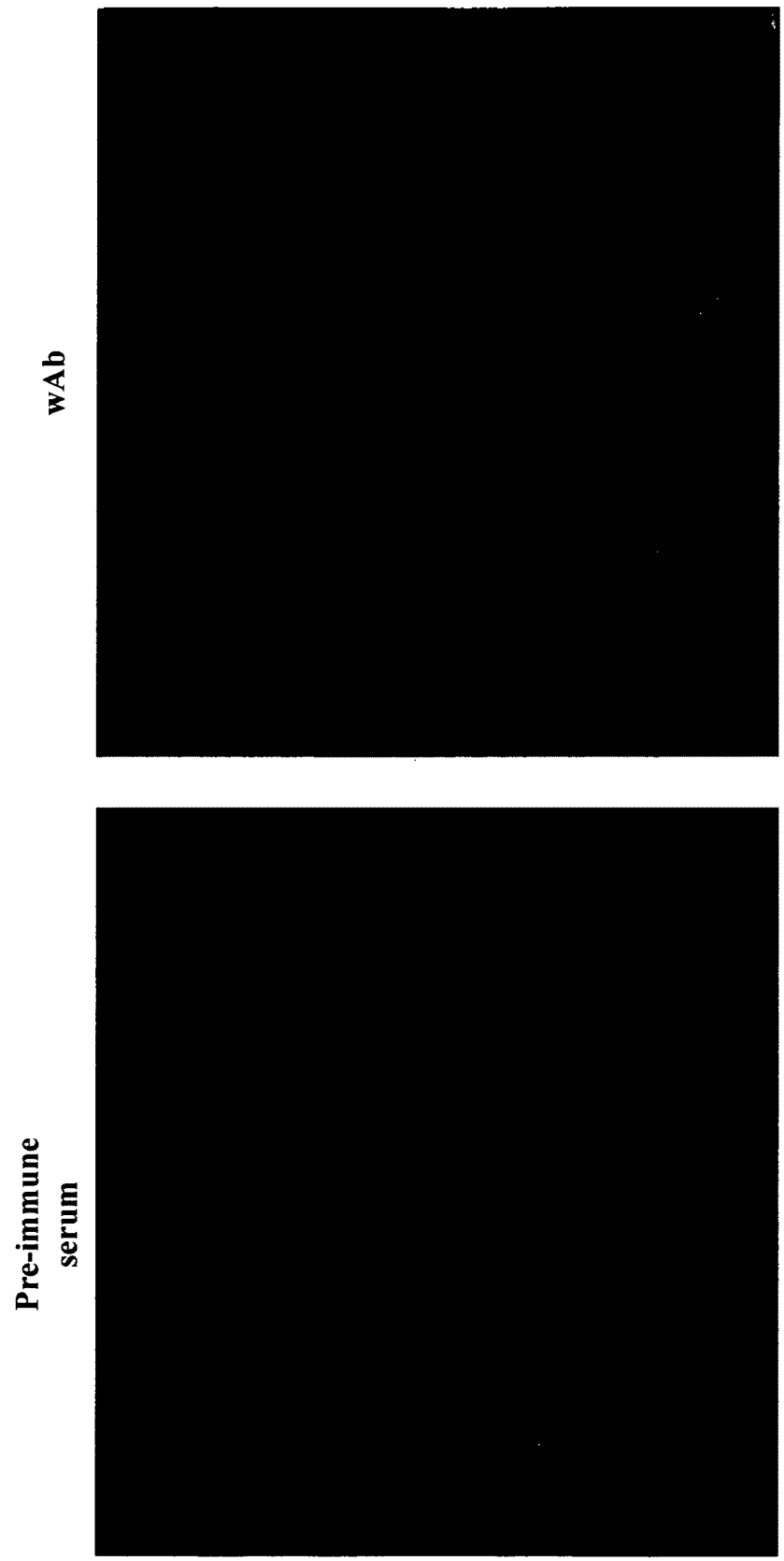
FIG. 4 depicts confocal imaging of sample from acute rats, day 2; preimmune vs. *Campylobacter jejuni* in accordance with various embodiments of the present invention.
Figure 5:
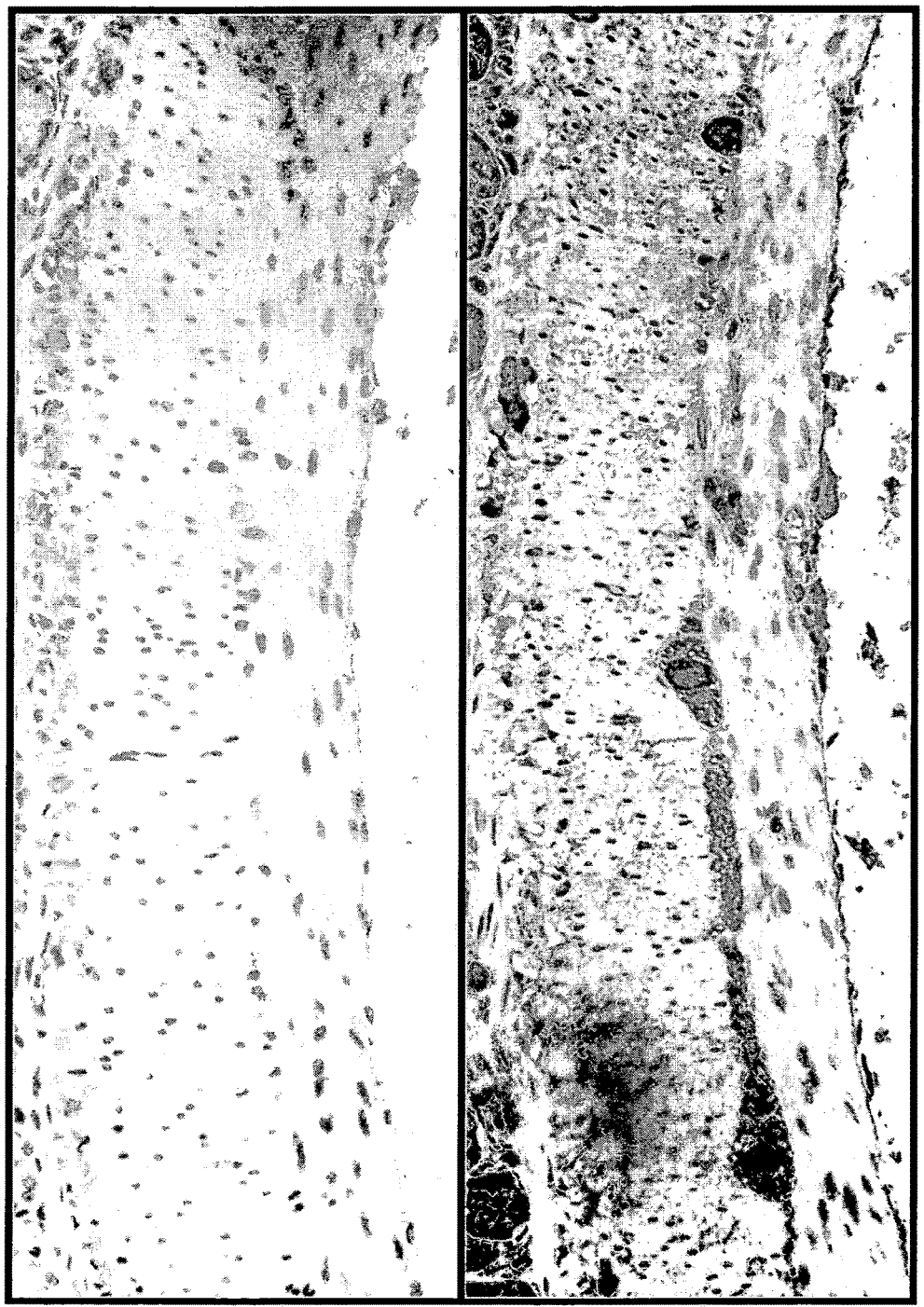
FIG. 5 depicts immunohistochemistry of control sample in accordance with various embodiments of the present invention.
Figure 6:
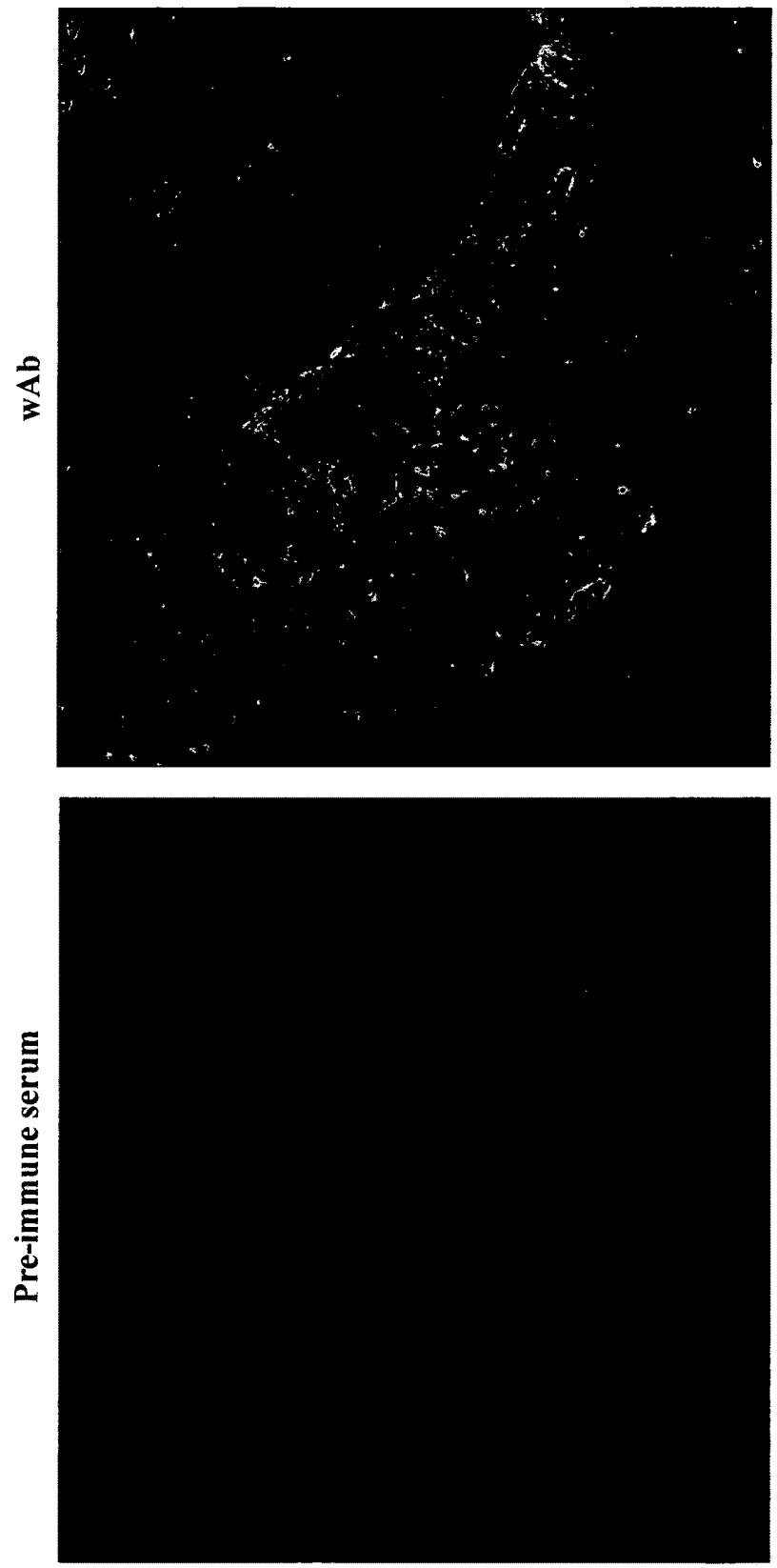
FIG. 6 depicts confocal imaging of control sample; preimmune vs. *Campylobacter jejuni* in accordance with various embodiments of the present invention.

Two groups of rats were compared in this study using immunostaining. In FIGS. 3a and b, rat ileum was examined 2 days after gavage with live *C. jejuni* 81-176. Pre-immune serum produced no staining Rats exposed to *C. jejuni* 81-176 with active infection demonstrated extensive staining for wAb which included mucosal surface and crypts. Deep tissue components most identified were the myenteric ganglia, interstitial cells of Cajal and other neural structures. Identical localization was seen with the immunofluorescent technique (FIGS. 4a and b). However, the same pattern was seen with both immunohistochemistry (FIGS. 5a and b) and immunofluorescence (FIGS. 6a and b) for rats that were never exposed to *C. jejuni*. This suggested the antibody to CdtB was cross reacting with a native rat protein most prominently located in the area of gut neural elements suggesting molecular mimicry.

Example 16

Immunohistochemical Localization of Anti-CdtB in Human Ileum

Figure 7:
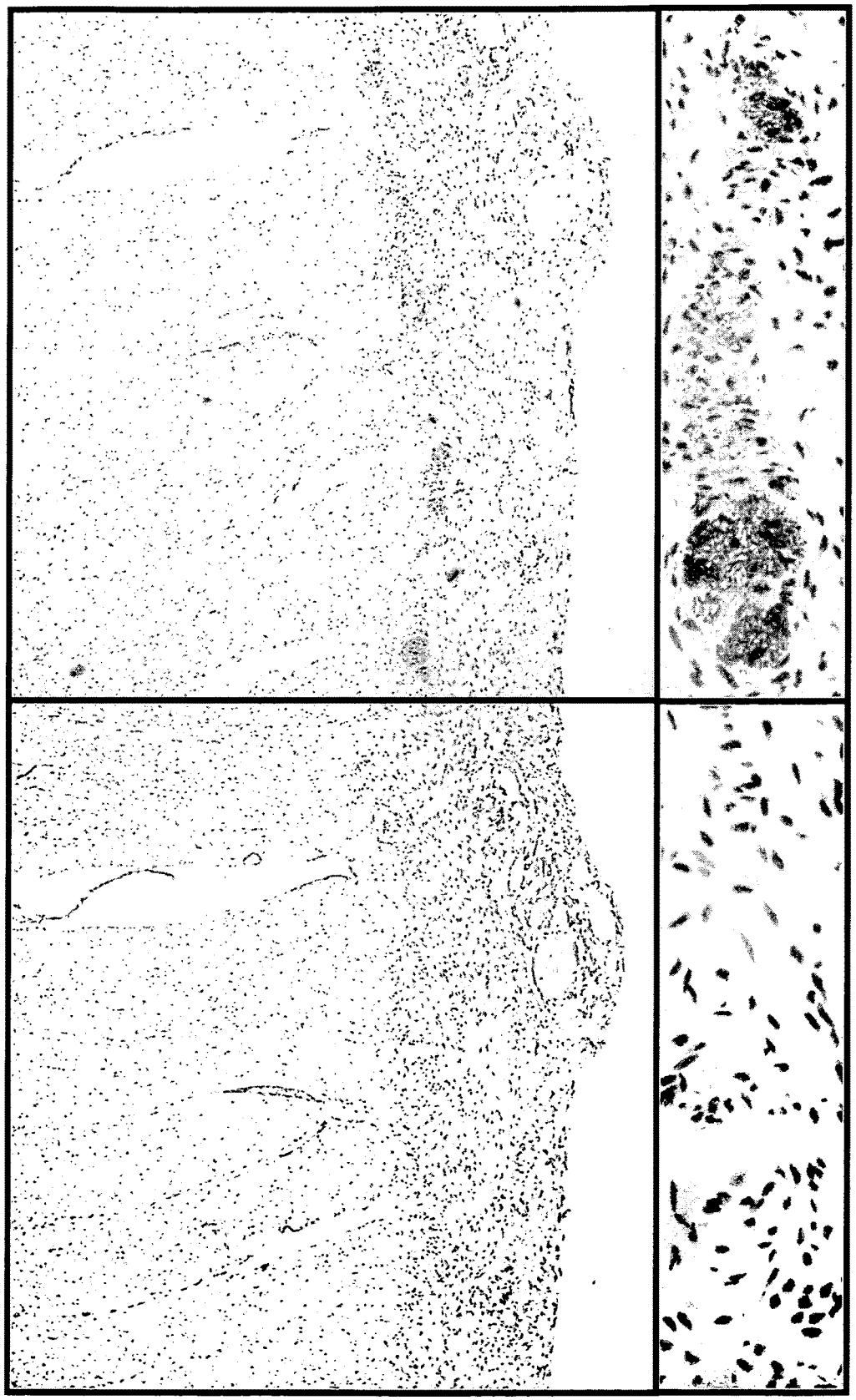
FIG. 7 depicts immunohistochemistry of human samples in accordance with various embodiments of the present invention.

Using human full thickness ileal tissue on immunohistochemistry, wAb again appeared to localize to the neural elements of the myenteric plexus (FIGS. 7a and b). Since these subjects were not IBS subject, the antibody to CdtB was assumed to be binding to a native protein.

Example 17

Colocalization of anti-CdtB with other neural markers

Figure 8:
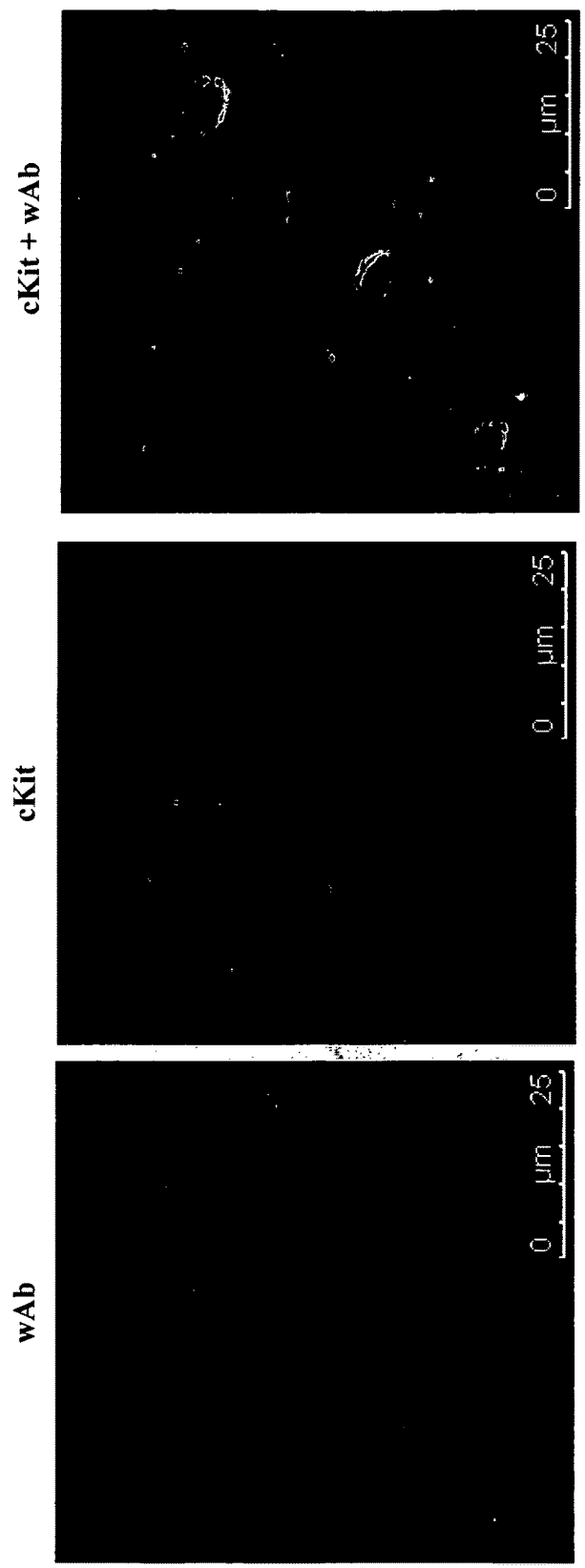
FIG. 8 depicts confocal imaging of control sample, ckit, and colocalization in accordance with various embodiments of the present invention.
Figure 9:
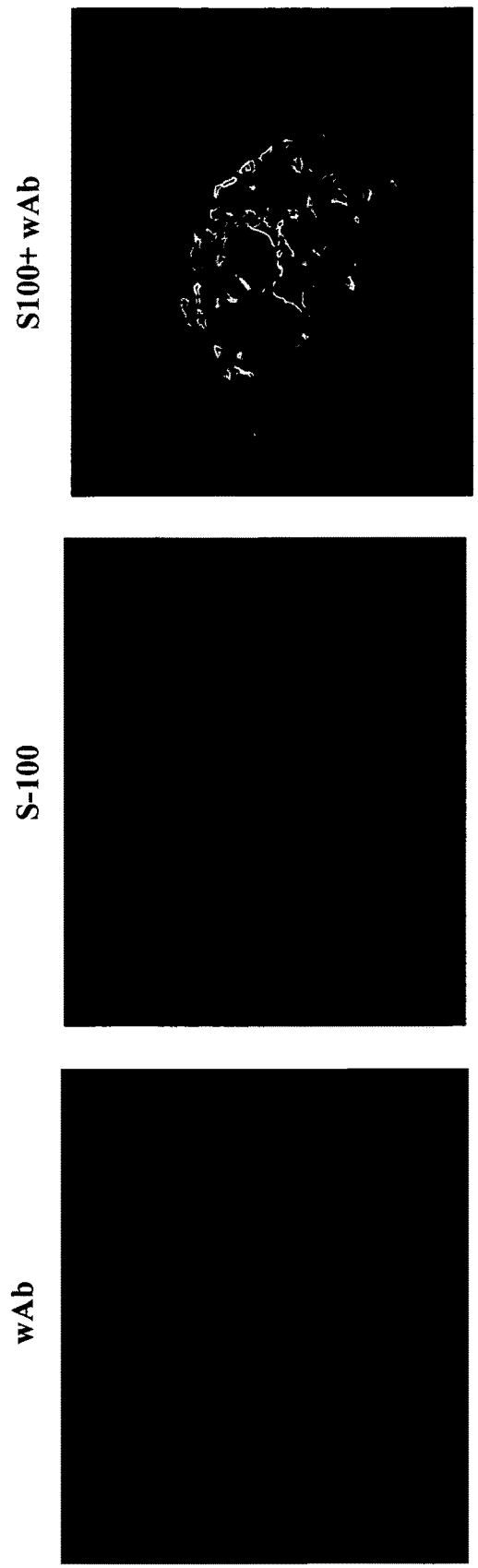
FIG. 9 depicts confocal imaging of control sample, s100, and colocolization in accordance with various embodiments of the present invention.

To demonstrate the specificity for mimicry to components of the enteric nervous system, 3 antibody markers (S-100 for enteric neurons, PGP 9.5 for ganglia and anti-c-kit for ICC) were compared to the wAb anti-CdtB antibody. From studies in all groups of rats including control rats, anti-CdtB co-localized both to ICC (with c-kit) (FIGS. 8a-c), neurons (FIGS. 9a-c) (with S-100). While co-localized, the staining for c-kit is a cell membrane stain and S-100 a nuclear stain. The anti-CdtB wAb appeared localized to the cytosolic component of the enteric neuronal cells (both ICC and neurons).

Example 18

Validating Molecular Mimicry in Humans

Figure 10:
FIG. 10 depicts confocal imaging of human, S100, and colocolization in accordance with various embodiments of the present invention.
Figure 11:
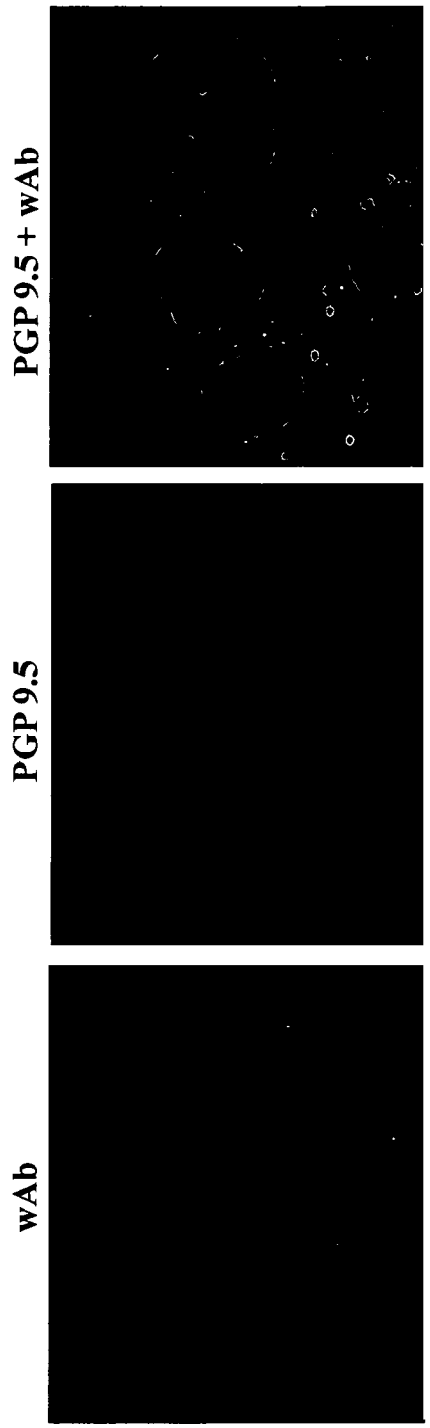
FIG. 11 depicts confocal imaging of human, PGP 9.5, and colocolization in accordance with various embodiments of the present invention.

To evaluate the potential for anti-CdtB wAb to demonstrate molecular mimicry in human small bowel, full thickness sections of ileum from right hemicolectomy specimens were mounted and stained as in the rats above. Similar to rats, colocalization was seen in with c-kit, S-100 (FIGS. 10a-c) and PGP 9.5 (FIGS. 11a-c).

Example 19

Molecular Mimicry Towards a Cytosolic Protein of Enteric Neurons

Figure 12:
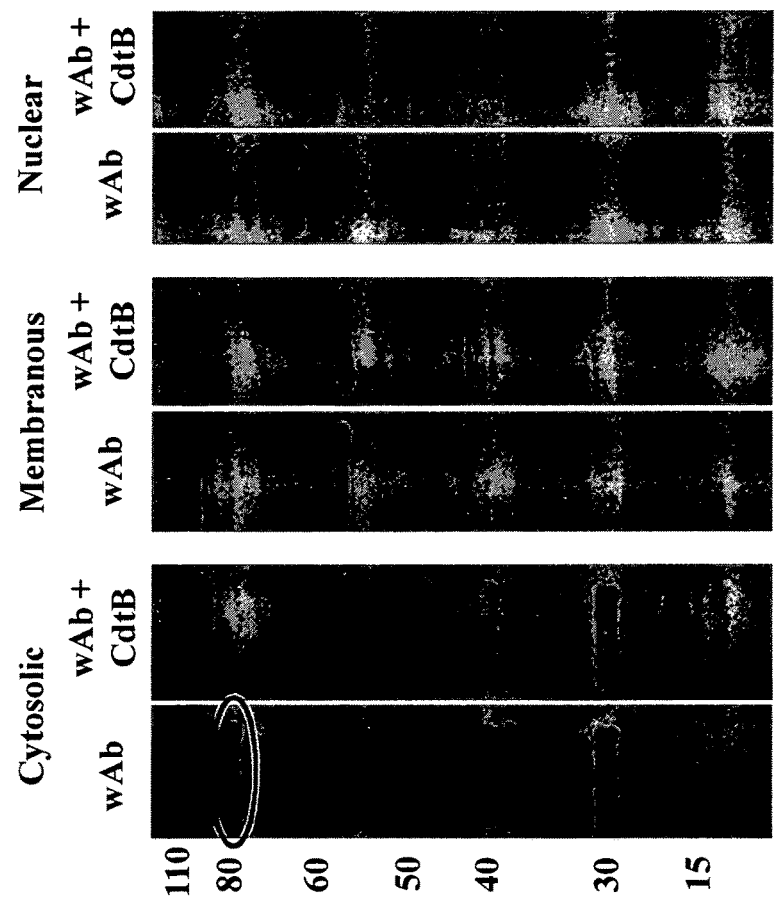
FIG. 12 depicts Western blot of fractionation & block in accordance with various embodiments of the present invention.
Figure 13:
FIG. 13 depicts confocal imaging of human, vinculin, and colocolization in accordance with various embodiments of the present invention.

Using lysates of enteric neuronal stem cells, wAb anti-CdtB antibodies demonstrate a band at 117 kDa (FIGS. 12 a and c). In fractionating the lysates, the 117 kDa band was located in the cytosolic fraction of the lysate (FIG. 12a). Blocking experiments using whole CdtB to block the antibody blocks binding to this 117 kDa protein (FIG. 12a). Mass spectroscopy identified the protein candidate in this band as vinculin. In the human tissue, confocal microscopy demonstrates colocalization of vinculin and wAb (FIGS. 13a-c).

Example 20

Demonstration of Anti-CdtB In Vivo in Rat Model of IBS

Figure 14:
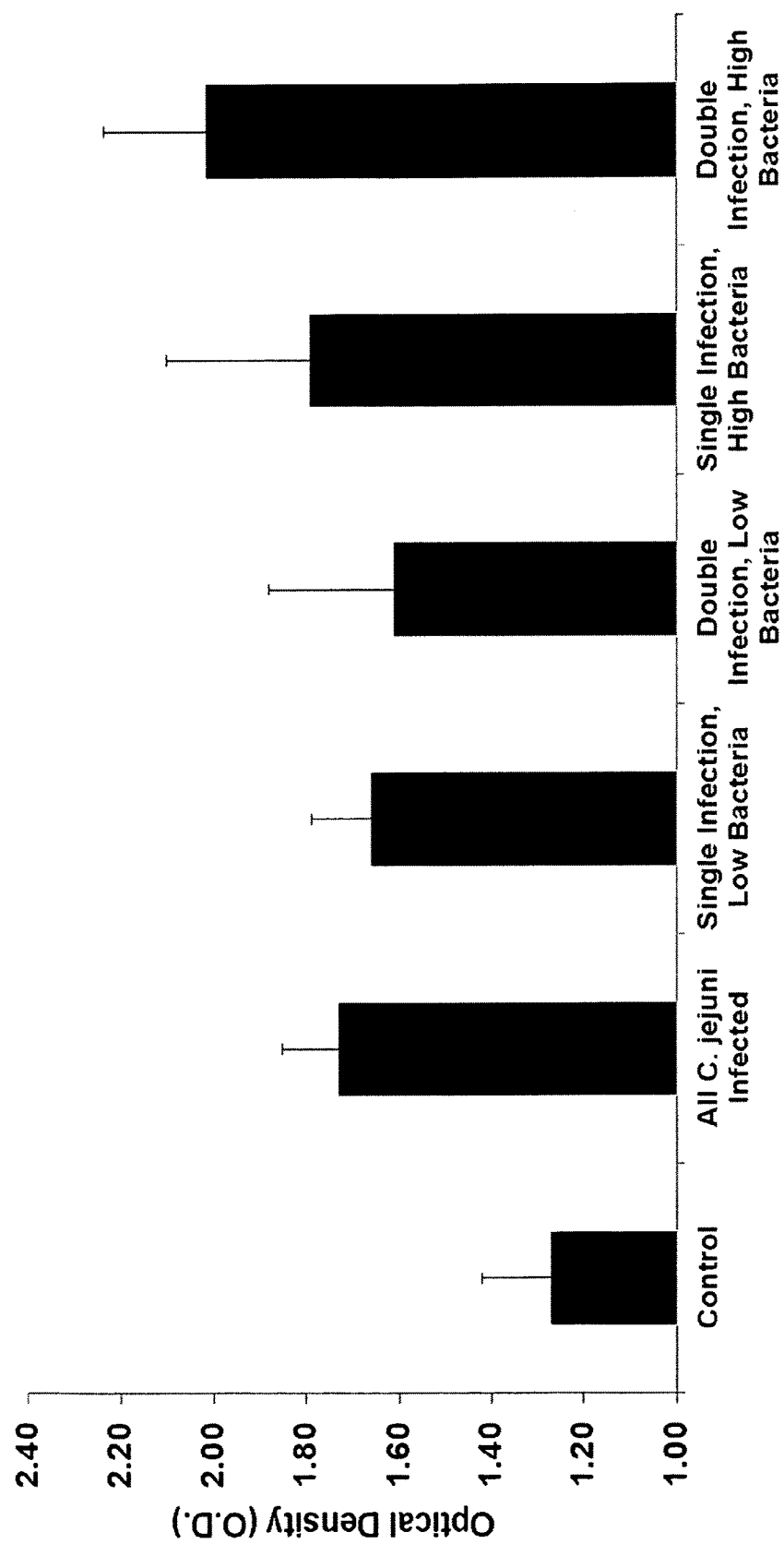
FIG. 14 depicts a difference between high and low bacteria counts in small bowel of rats in accordance with various embodiments of the present invention.
Figure 15:
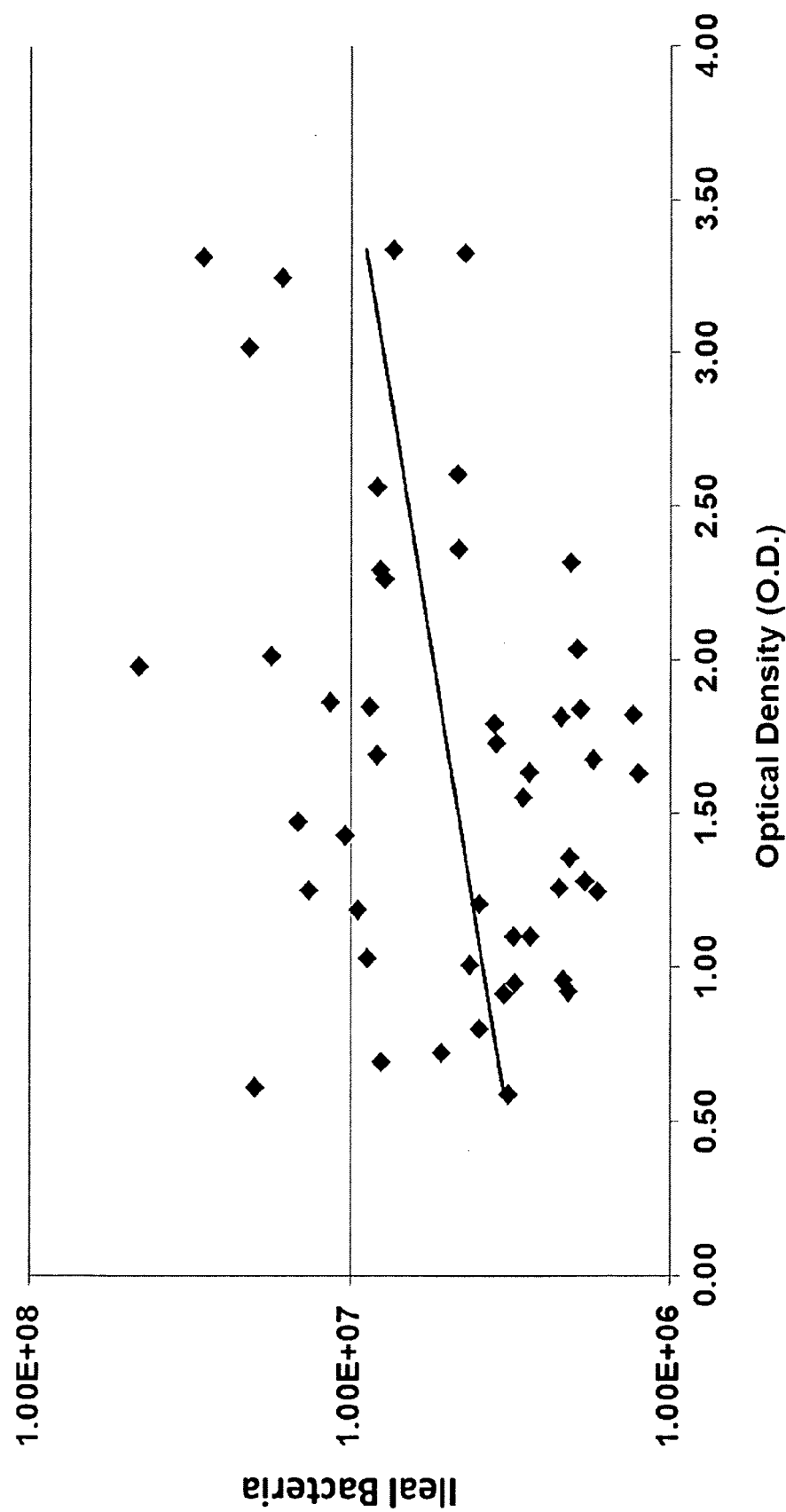
FIG. 15 depicts a comparison between antibody titers and SIBO levels (r=0.3, P=0.04) in accordance with various embodiments of the present invention.

To demonstrate the role of antibodies to CdtB in the phenotype of post-infectious IBS, an ELISA was developed using C. jejuni anti-CdtB. In this study, control rats, rats with single exposure to C. jejuni and rats with two exposures to C. jejuni, 2 months apart, were tested and compared to the outcome of small intestinal bacterial overgrowth by PCR of small bowel enteric flora. In FIG. 14 it is apparent that anti-CdtB was not only dependent on the previous infection with C. jejuni but also the development of small intestinal bacterial overgrowth. Among rats receiving C. jejuni, those with bacterial overgrowth had higher titers of anti-CdtB than those with no bacterial overgrowth irrespective of number of infections with C. jejuni. This is further demonstrated by the significant correlation between circulating anti-CdtB and greater degree of small intestinal bacterial overgrowth based on qPCR of total bacteria (FIG. 15).

Example 21

Demonstration of Anti-CdtB and Anti-Vinculin in Humans with Post-Infectious IBS

Figure 16:
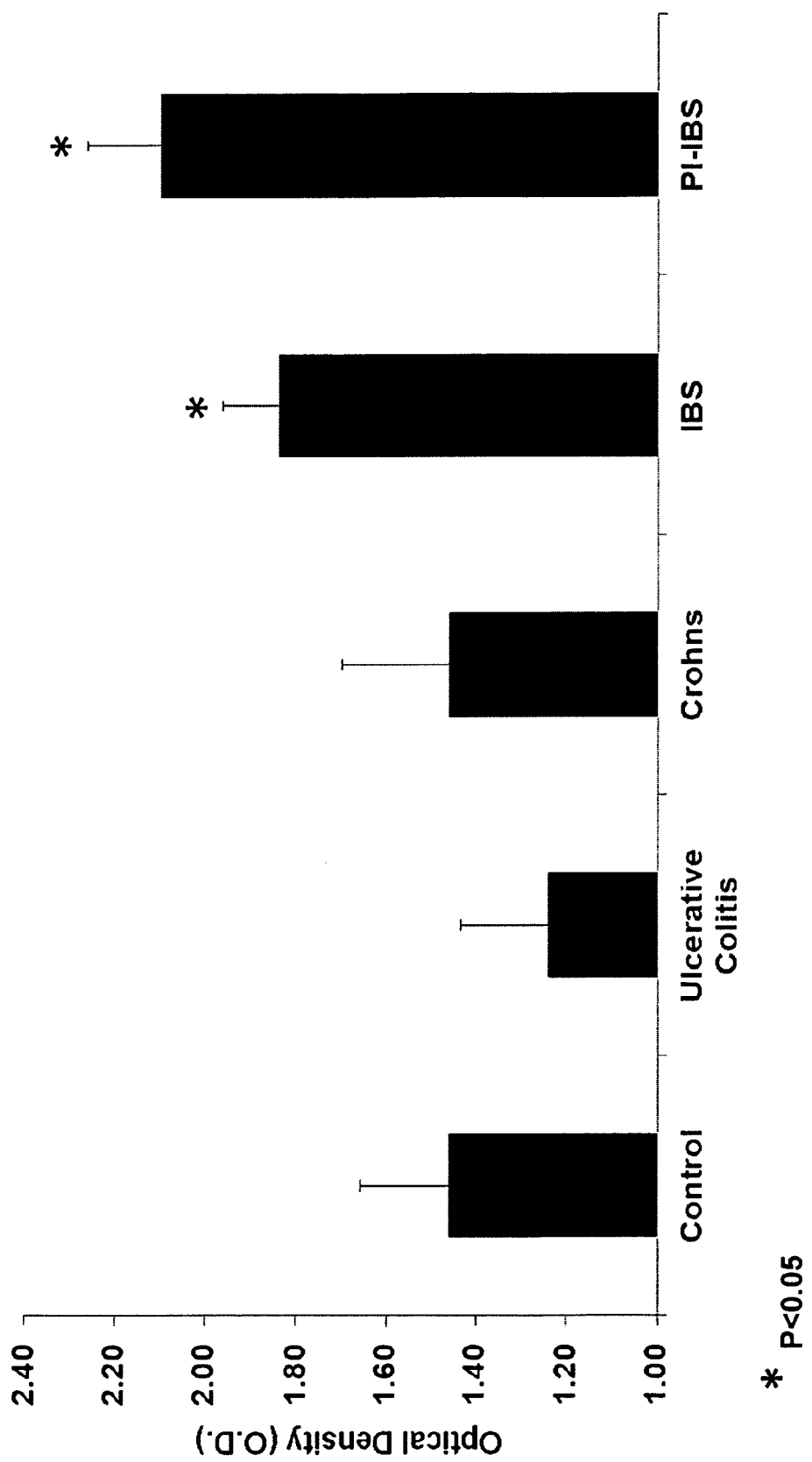
FIG. 16 depicts cdtB antibodies in human serum in accordance with various embodiments of the present invention.

In this final experiment, serum was collected from 43 humans with IBS, 20 healthy subjects and 20 subjects with inflammatory bowel disease (10 subjects with Crohn's disease and 10 subjects with ulcerative colitis). Using absolute values, subjects with IBS had the greater titer of anti-CdtB antibodies compared to IBD or controls (FIG. 16) Using an OD>2 as a diagnosis of IBS and post-infectious IBS, this threshold was able to identify IBS with a sensitivity of 85.7% and specificity of 67.2% in comparison to inflammatory bowel disease (Table 1b).

TABLE 1b

Test dynamics of anti-CdtB to diagnose IBS

| | | ELISA Positive | |
| --- | --- | --- | --- |
| | | Yes | No |
| IBS vs. IBD | IBS | 18 | 20 |
| | IBD | 3 | 17 |
| Test Characteristics | Sensitivity | 85.7% | |
| | Specificity | 67.2% | |

Figure 17:
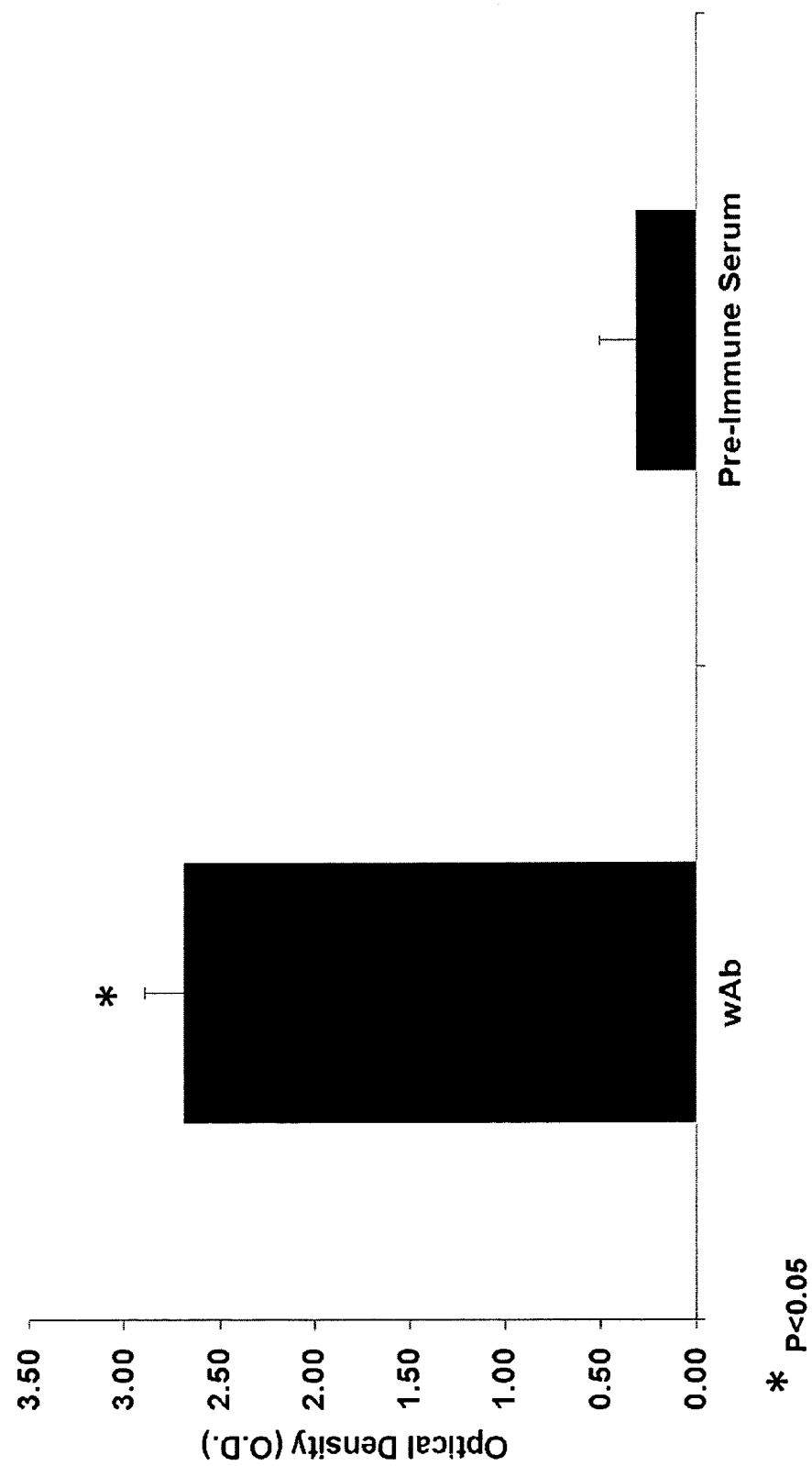
FIG. 17 depicts cdtB and pre-immune serum vs. vinculin protein in accordance with various embodiments of the present invention.
Figure 18:
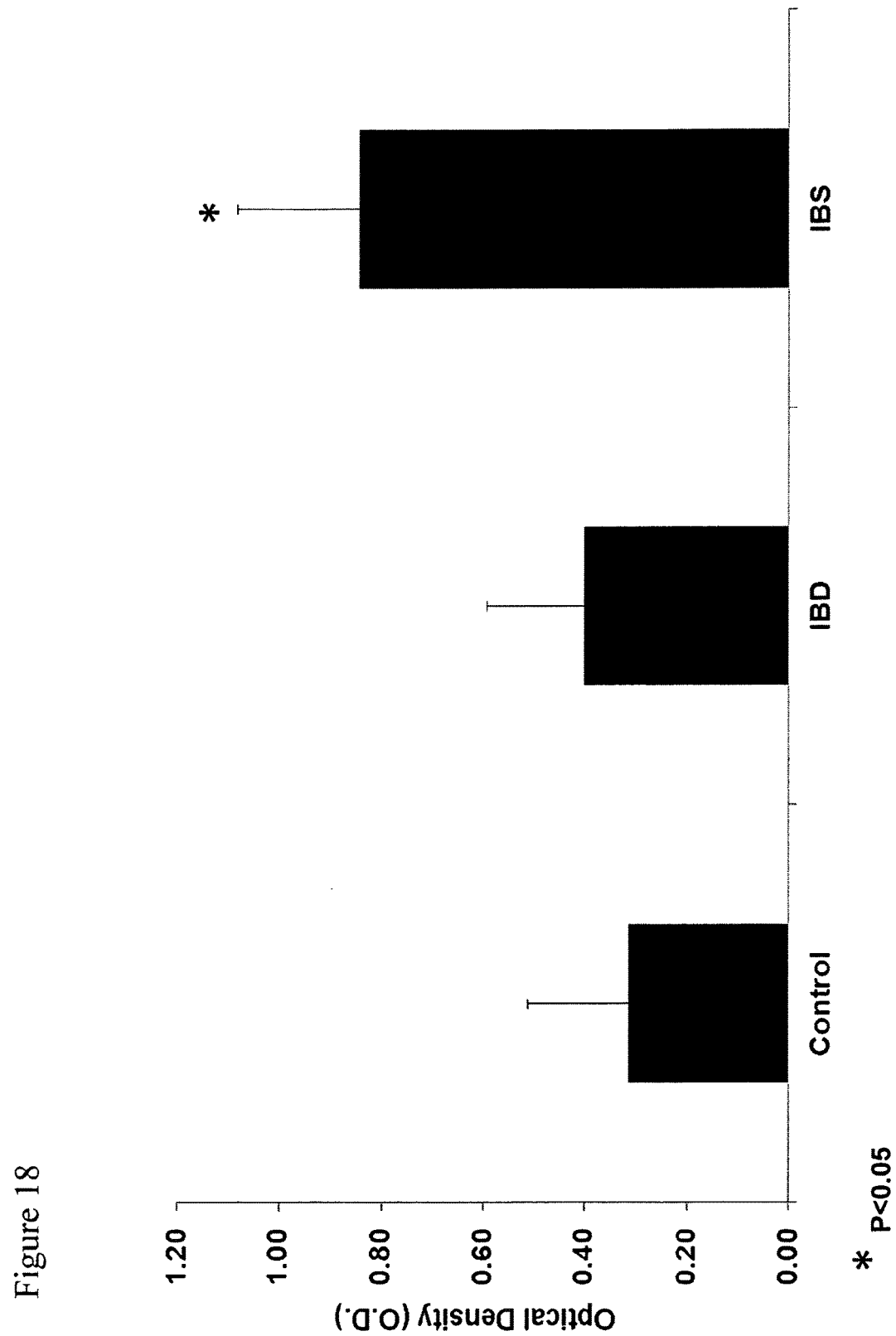
FIG. 18 depicts vinculin antibodies in human serum in accordance with various embodiments of the present invention.

Using vinculin as the ELISA substrate, applying pre-immune serum to the wells produced a very low response. However, the application of wAb to the wells produced a vigorous response. This suggested that anti-CdtAb strongly react to vinculin in the ELISA (FIG. 17). When ELISA testing for vinculin was conducted using serum from the three human groups, again there was significantly higher titers of anti-vinculin in IBS subjects.

Finally, ELISA using latrophillin or c-kit demonstrated no difference between IBS, controls and subjects with inflammatory bowel disease suggesting the differences were not due to non-specific binding (data not shown).

Example 22

Circulating Antibodies to Cytolethal Distending Toxin B Correlates with the Development of Small Intestinal Bacterial Overgrowth in a Rat Model of Post-Infectious IBS The level of serum anti-CdtB antibodies in the rat model of post-infectious IBS was examined and correlated with the development of SIBO.

Methods: Male Sprague-Dawley rats (n=100) were obtained as infants and randomized to three groups. The first group was gavaged with C. jejuni 81-176 ($10^8$ cfu/mL) as juveniles and two months later as adults (J+/A+). The second group was gavaged with C. jejuni only as adults (J−/A+). The third group was never exposed to C. jejuni (controls). Three months after the adult infection all rats were euthanized. After euthanasia, segments of ileum, jejunum and duodenum were ligated and removed as previously described (Chatterjee, et al). From each bowel segment, DNA was extracted from luminal contents and qPCR using universal bacterial primers was used to determine the presence or absence of SIBO. SIBO was defined as bacterial counts in excess of 2 standard deviations above mean of controls for each segment. At euthanasia, blood was taken and serum isolated. A 96 well plate was coated with CdtB to which rat serum was added and incubated for 90 minutes. Wells were washed and incubated with a fluorescent secondary antibody and read on a plate reader.

Results: ELISA for detection of anti-CdtB in serum of control rats demonstrated an optical density (OD) of 1.27±0.15. All rats exposed to C. jejuni had a greater OD of 1.73±0.12 (P<0.05). In the J−/A+ group, the single exposure to C. jejuni resulted in SIBO in 26% of rats. In J+/A+ double exposed rats, SIBO was seen in 46% (P<0.05). Anti-CdtB was greater if rats had SIBO irrespective of whether they had a single (1.79±0.31) or double exposure (2.02±0.22) to C. jejuni. Rats that did not have SIBO had titers <1.7. Plotting the level of bacteria in the ileum against the ELISA findings demonstrated a correlation between levels of bacteria and anti-CdtB (R=0.3, P<0.05).

Conclusions: Antibodies to CdtB develop after exposure to C. jejuni but appear to develop in a pattern that relates to the development of SIBO more than the number of exposures to C. jejuni. Based on the affinity for ICC and ganglia, the inventors believe that these antibodies are important to the pathophysiology of IBS perhaps by affecting gut motor function leading to SIBO.

Example 23

Antibodies to Cytolethal Distending Toxin B and Auto-Antibodies to Human Vinculin are Elevated in IBS Subjects In an animal model of post-infectious IBS, antibodies to CdtB bind neurological elements in the gut wall including interstitial cells of Cajal (ICC) and ganglia through a process of molecular mimicry/autoimmunity. The protein on these nerves to which this mimicry occurs was found to be vinculin, and antibodies to vinculin predict SIBO in rats. The inventors translate these antibody tests to humans to determine the titers of anti-CdtB and anti-vinculin antibodies in the serum of subjects with IBS and inflammatory bowel disease (IBD).

Methods: Consecutive IBS subjects meeting Rome III criteria were recruited from a GI Motility clinic (n=45). In addition, 30 subjects with IBD were recruited from a tertiary care IBD clinic. Finally, 20 healthy controls were identified based on a negative symptom questionnaire. All subjects were consented and serum samples were obtained. An enzyme-linked immunosorbent assay (ELISA) was created by coating 96 well plates with either 0.4 µg of recombinant vinculin or 0.4 µg/mL of purified CdtB per well. Serum from each subject was added to the wells and incubated for 90 minutes. The wells were washed and then secondary antibodies were added to each well. The optical density (OD) measures were determined using a plate reader.

Results: In plates coated with CdtB, the mean OD for IBS serum was 1.89±0.12. This was significantly greater than for subjects with IBD (1.35±0.22) (P<0.05) or healthy controls (1.46±0.20) (P<0.05). In plates coated with vinculin, the mean OD for IBS serum was 0.53±0.07. This was significantly greater than for subjects with IBD (0.21±0.09) (P<0.05). There was a trend for a difference from healthy controls (0.31±0.10) (P=0.11). There was no difference between IBS-C or IBS-D for either antibody.

Conclusions: Both anti-CdtB and autoimmune anti-vinculin antibodies are detectable in IBS subjects and are seen to be elevated in IBS compared to controls and IBD. The detection of anti-CdtB and anti-vinculin suggest new clues to the diagnosis and pathophysiology of IBS. This is the first study to link acute gastroenteritis to an autoimmune process in IBS.

Example 24

Molecular Mimicry Leads to Autoimmunity to Vinculin in Humans: The Missing Link in the Pathophysiology of IBS The inventors investigate the human antigen to which anti-CdtB binds.

Methods: First, non-IBS human full thickness ileal tissue (from right hemicolectomy) was obtained. Ileal sections were incubated with purified rabbit antibodies to CdtB, washed and incubated with fluorescent secondary antibodies. Colocalization studies were performed with anti-c-kit (specific for ICC), S-100 (specific for neurons) and PGP 9.5 (specific for ganglia). Next, immunoprecipitation was performed by generating a column with anti-CdtB through which a lysate of human enteric neuronal cells (Emory University) was passed. Anti-CdtB adherent protein was eluted and two western blots were performed. One was incubated with anti-CdtB and the other with anti-CdtB pre-incubated with CdtB protein (blocking peptide). A band was identified at 117 kDa, purified and identified by mass spectroscopy as human vinculin. An aliquot of 0.4 ug of commercial vinculin was coated per well in 96 well plates. Anti-CdtB was added to one series of wells, and anti-CdtB mixed with whole CdtB protein (blocking peptide) to another.

Results: Using full-thickness human ileal tissue, anti-CdtB was specific for ICC and ganglia. This was based on colocalization of anti-CdtB with anti-c-kit, PGP 9.5 and S-100 (see figure). Thus anti-CdtB appeared to be interacting with a human protein on ICCs and ganglia. Based on immunoprecipitation, a protein band was identified at 117 kDa. Using mass spectroscopy this protein was identified as human vinculin. Subsequently, human vinculin was obtained commercially and by ELISA, anti-CdtB had a high affinity for human vinculin but not the control peptide. Binding to vinculin was blocked by the CdtB peptide.

Conclusions: In the pathophysiology of post-infectious IBS, subjects develop antibodies to CdtB which have cross reactivity through molecular mimicry to vinculin, a cell membrane cytoskeletal protein important in neural cell migration and adherence. Given our emerging data of reduced vinculin levels in post-infectious rats, molecular mimicry to vinculin may be important to the cause of SIBO and IBS through effects on ICC and ganglia.

Example 25

Vinculin Expression is Reduced in an Animal Model of Post-Infectious IBS

The inventors assess vinculin expression in the post-infectious rat model.

Methods: Sprague-Dawley rats were divided into 3 groups. Group 1 rats served as controls (n=20). Group 2 rats were gavaged with $10^8$ cfu/mL C. jejuni as adults (J−/A+). Group 3 rats were gavaged with C. jejuni as juveniles and then again 2 months later a second time as adults. For infected rats, they were euthanized 3 months after clearance of C. jejuni. At the time of euthanasia, sections of small bowel (duodenum, jejunum, and ileum) were ligated and contents for total bacterial contents by qPCR as previously described. A segment of mid small bowel was also obtained and retained in RNA later. After homogenizing, extraction of RNA and conversion to cDNA, qPCR was used to determine the level of vinculin in the bowel wall after normalizing for β-actin. The level of vinculin was assessed based on the number of C. jejuni infections and the presence or absence of SIBO in this animal model.

Results: Based on normal bacterial levels in the small bowel segments of normal subjects, SIBO was identified in 26% and 46% of rats with single and double exposure to C. jejuni. Overall, vinculin expression was reduced in small bowel of rats exposed to C. jejuni (0.058±0.0053) compared to control rats (0.087±0.0053) (P<0.001). Furthermore, there was a greater reduction of vinculin with two exposures to C. jejuni compared to a single exposure (see figure) (P<0.0001). There was also a trend to lower vinculin expression in rats with SIBO (P=0.05).

Conclusions: Vinculin expression is reduced by exposure to C. jejuni. This reduction is dependent on the number of exposures to C. jejuni with greater reduction in rats that have been exposed to C. jejuni twice. Finally, SIBO is associated with a lower level of vinculin expression. Vinculin may be important in the pathogenesis of post-infectious IBS.

Example 26

Subjects (18-65 yrs) with Rome positive IBS were recruited from Cedars-Sinai Medical Center and Beth Israel Deaconess Medical Center. Subjects were assessed for symptoms and demographics followed by collection of sera. Subjects were excluded if they had concomitant GI disease, previous GI surgery, adhesions, unstable thyroid disease, diabetes, or HIV. Healthy controls were recruited based on the completion of a GI symptom questionnaire. On this questionnaire, subjects had to have marked <10 for bloating, diarrhea, abdominal pain, and constipation inclusive on a 0-100 VAS. Subjects with inflammatory bowel disease were recruited from an expert tertiary care medical center. Subjects with Crohn's disease or ulcerative colitis were excluded if there was a history of biologic therapy and current prednisone use. Serum from all 3 groups was used to perform and ELISA to determine antibodies to human recombinant vinculin.

Figure 19:
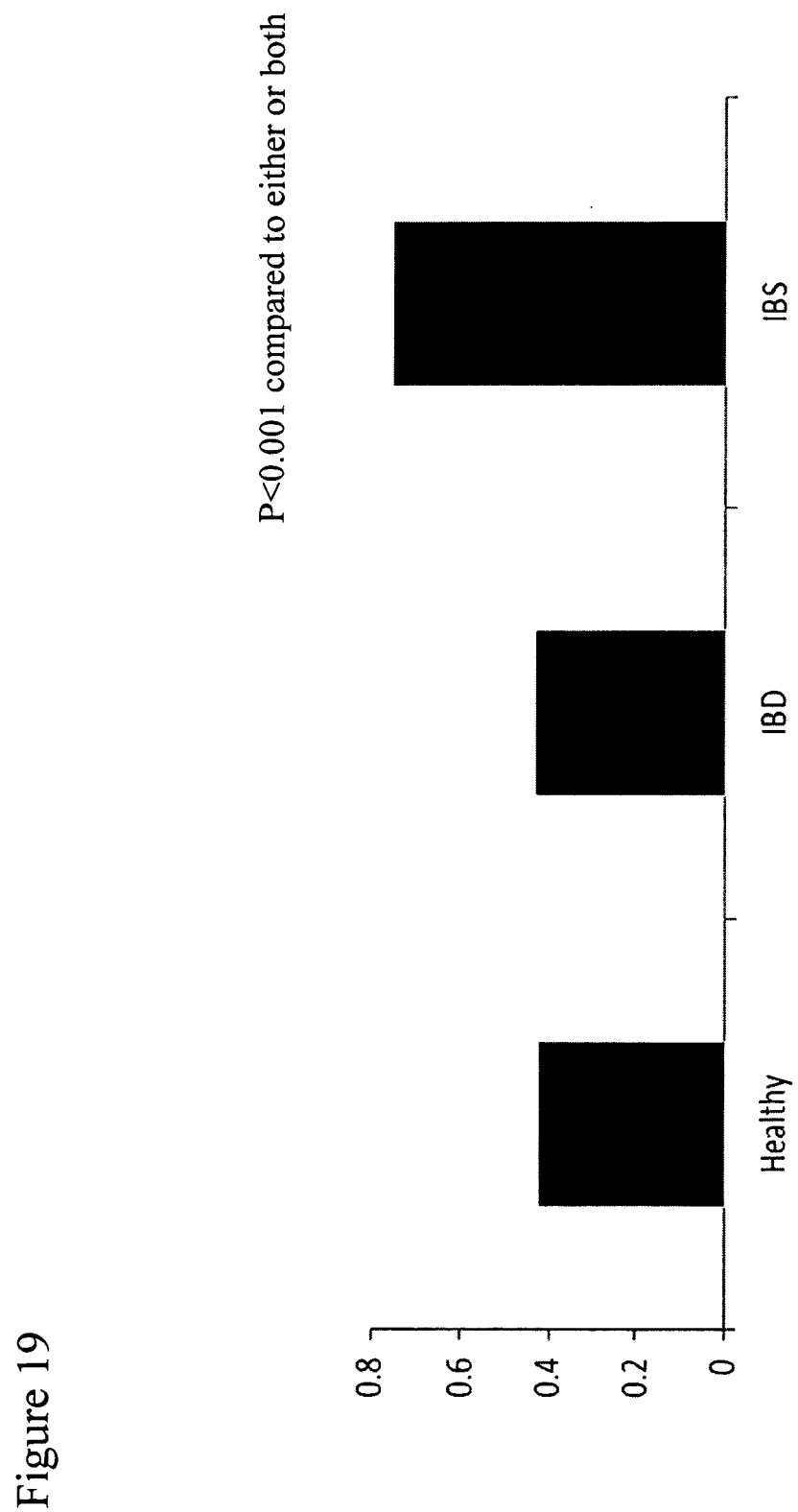
FIG. 19 depicts titer of antibodies that were measured in IBS, IBD and healthy controls. IBS subjects had the highest level of antibody in accordance with various embodiments of the present invention. The y axis is the optical density (OD) of the ELISA test.

In total 165 IBS, 30 IBD and 26 healthy control subjects were evaluated. Demographics were similar between groups. Overall, IBS had a significantly greater optical density in the ELISA for anti-vinculin antibodies compared to IBD and healthy subjects. (FIG. 19) Comparing the two major centers for IBS recruitment, results from both centers were similarly abnormal (P=NS). Interestingly, subjects with a history of acute gastroenteritis, even higher levels of antibodies were seen (P<0.05).

Anti-vinculin antibodies are elevated in IBS compared to non-IBS. This is the first diagnostic test for IBS based on serum and a pathophysiologic mechanism of IBS through acute gastroenteritis precipitated molecular mimicry and autoimmunity.

REFERENCES

1. Drossman, D. A., Camilleri, M., Mayer, E. A., and Whitehead, W. E. 2002. AGA technical review on irritable bowel syndrome. *Gastroenterology* 123:2108-2131.
2. Pimentel, M. 2010. Evaluating a bacterial hypothesis in IBS using a modification of Koch's postulates: part 1. *Am J Gastroenterol* 105:718-721.
3. Pimentel, M., Lembo, A., Chey, W. D., Zakko, S., Ringel, Y., Yu, J., Mareya, S. M., Shaw, A. L., Bortey, E., and Forbes, W. P. 2011. Rifaximin therapy for patients with irritable bowel syndrome without constipation. *N Engl J Med* 364:22-32.
4. Halvorson, H. A., Schlett, C. D., and Riddle, M. S. 2006. Postinfectious irritable bowel syndrome—a meta-analysis. *Am J Gastroenterol* 101:1894-1899; quiz 1942.
5. Thabane, M., Kottachchi, D. T., and Marshall, J. K. 2007. Systematic review and meta-analysis: The incidence and prognosis of post-infectious irritable bowel syndrome. *Aliment Pharmacol Ther* 26:535-544.
6. Spiller, R. C., Jenkins, D., Thornley, J. P., Hebden, J. M., Wright, T., Skinner, M., and Neal, K. R. 2000. Increased rectal mucosal enteroendocrine cells, T lymphocytes, and increased gut permeability following acute *Campylobacter* enteritis and in post-dysenteric irritable bowel syndrome. *Gut* 47:804-811.
7. Mearin, F., Perez-Oliveras, M., Perello, A., Vinyet, J., Ibanez, A., Coderch, J., and Perona, M. 2005. Dyspepsia and irritable bowel syndrome after a *Salmonella* gastroenteritis outbreak: one-year follow-up cohort study. *Gastroenterology* 129:98-104.
8. Okhuysen, P. C., Jiang, Z. D., Carlin, L., Forbes, C., and DuPont, H. L. 2004. Post-diarrhea chronic intestinal symptoms and irritable bowel syndrome in North American travelers to Mexico. *Am J Gastroenterol* 99:1774-1778.
9. Ji, S., Park, H., Lee, D., Song, Y. K., Choi, J. P., and Lee, S. I. 2005. Post-infectious irritable bowel syndrome in patients with *Shigella* infection. *J Gastroenterol Hepatol* 20:381-386.
10. Pimentel, M., Chatterjee, S., Chang, C., Low, K., Song, Y., Liu, C., Morales, W., Ali, L., Lezcano, S., Conklin, J., et al. 2008. A new rat model links two contemporary theories in irritable bowel syndrome. *Dig Dis Sci* 53:982-989.
11. Brint, E. K., MacSharry, J., Fanning, A., Shanahan, F., and Quigley, E. M. 2011. Differential expression of toll-like receptors in patients with irritable bowel syndrome. *Am J Gastroenterol* 106:329-336.
12. Langhorst, J., Junge, A., Rueffer, A., Wehkamp, J., Foell, D., Michalsen, A., Musial, F., and Dobos, G. J. 2009. Elevated human beta-defensin-2 levels indicate an activation of the innate immune system in patients with irritable bowel syndrome. *Am J Gastroenterol* 104:404-410.
13. Liebregts, T., Adam, B., Bredack, C., Roth, A., Heinzel, S., Lester, S., Downie-Doyle, S., Smith, E., Drew, P., Talley, N. J., et al. 2007. Immune activation in patients with irritable bowel syndrome. *Gastroenterology* 132:913-920.
14. Scully, P., McKernan, D. P., Keohane, J., Groeger, D., Shanahan, F., Dinan, T. G., and Quigley, E. M. 2010. Plasma cytokine profiles in females with irritable bowel syndrome and extra-intestinal co-morbidity. *Am J Gastroenterol* 105:2235-2243.
15. Dinan, T. G., Clarke, G., Quigley, E. M., Scott, L. V., Shanahan, F., Cryan, J., Cooney, J., and Keeling, P. W. 2008. Enhanced cholinergic-mediated increase in the pro-inflammatory cytokine IL-6 in irritable bowel syndrome: role of muscarinic receptors. *Am J Gastroenterol* 103:2570-2576.
16. Barkhordari, E., Rezaei, N., Ansaripour, B., Larki, P., Alighardashi, M., Ahmadi-Ashtiani, H. R., Mahmoudi, M., Keramati, M. R., Habibollahi, P., Bashashati, M., et al. 2010. Proinflammatory cytokine gene polymorphisms in irritable bowel syndrome. *J Clin Immunol* 30:74-79.
17. Villani, A. C., Lemire, M., Thabane, M., Belisle, A., Geneau, G., Garg, A. X., Clark, W. F., Moayyedi, P., Collins, S. M., Franchimont, D., et al. 2010. Genetic risk factors for post-infectious irritable bowel syndrome following a waterborne outbreak of gastroenteritis. *Gastroenterology* 138:1502-1513.
18. Taylor, D. N., Echeverria, P., Pitarangsi, C., Seriwatana, J., Bodhidatta, L., and Blaser, M. J. 1988. Influence of strain characteristics and immunity on the epidemiology of *Campylobacter* infections in Thailand. *J Clin Microbiol* 26:863-868.
19. Calva, J. J., Ruiz-Palacios, G. M., Lopez-Vidal, A. B., Ramos, A., and Bojalil, R. 1988. Cohort study of intestinal infection with *campylobacter* in Mexican children. *Lancet* 1:503-506.
20. Oberhelman, R. A., Gilman, R. H., Sheen, P., Taylor, D. N., Black, R. E., Cabrera, L., Lescano, A. G., Meza, R., and Madico, G. 1999. A placebo-controlled trial of *Lactobacillus* GG to prevent diarrhea in undernourished Peruvian children. *J Pediatr* 134:15-20.
21. Taylor, D. N., Perlman, D. M., Echeverria, P. D., Lexomboon, U., and Blaser, M. J. 1993. *Campylobacter* immunity and quantitative excretion rates in Thai children. *J Infect Dis* 168:754-758.
22. Coker, A. O., Isokpehi, R. D., Thomas, B. N., Amisu, K. O., and Obi, C. L. 2002. Human campylobacteriosis in developing countries. *Emerg Infect Dis* 8:237-244.
23. Sorokin, M., Usein, C. R., Irimia, M., and Damian, M. 2007. A laboratory-based survey of *Campylobacter* infections in Prahova County. *Roum Arch Microbiol Immunol* 66:85-89.
24. Morales, W., Pimentel, M., Hwang, L., Kunkel, D., Pokkunuri, V., Basseri, B., Low, K., Wang, H., Conklin, J. L., and Chang, C. 2011. Acute and Chronic Histological Changes of the Small Bowel Secondary to *C. jejuni* Infection in a Rat Model for Post-Infectious IBS. *Dig Dis Sci*.
25. Jee, S. R., Morales, W., Low, K., Chang, C., Zhu, A., Pokkunuri, V., Chatterjee, S., Soffer, E., Conklin, J. L., and Pimentel, M. 2010. ICC density predicts bacterial overgrowth in a rat model of post-infectious IBS. *World J Gastroenterol* 16:3680-3686.
26. Vantrappen, G., Janssens, J., Hellemans, J., and Ghoos, Y. 1977. The interdigestive motor complex of normal subjects and patients with bacterial overgrowth of the small intestine. *J Clin Invest* 59:1158-1166.
27. Nieuwenhuijs, V. B., Verheem, A., van Duijvenbode-Beumer, H., Visser, M. R., Verhoef, J., Gooszen, H. G., and Akkermans, L. M. 1998. The role of interdigestive small bowel motility in the regulation of gut microflora, bacterial overgrowth, and bacterial translocation in rats. *Ann Surg* 228:188-193.
28. Sarna, S. K. 2008. Are interstitial cells of Cajal plurifunction cells in the gut? *Am J Physiol Gastrointest Liver Physiol* 294:G372-390.
29. Der-Silaphet, T., Malysz, J., Hagel, S., Larry Arsenault, A., and Huizinga, J. D. 1998. Interstitial cells of cajal direct normal propulsive contractile activity in the mouse small intestine. *Gastroenterology* 114:724-736.
30. Malysz, J., Thuneberg, L., Mikkelsen, H. B., and Huizinga, J. D. 1996. Action potential generation in the small intestine of W mutant mice that lack interstitial cells of Cajal. *Am J Physiol* 271:G387-399.
31. Langton, P., Ward, S. M., Carl, A., Norell, M. A., and Sanders, K. M. 1989. Spontaneous electrical activity of interstitial cells of Cajal isolated from canine proximal colon. *Proc Natl Acad Sci USA* 86:7280-7284.
32. Ordog, T., Ward, S. M., and Sanders, K. M. 1999. Interstitial cells of cajal generate electrical slow waves in the murine stomach. *J Physiol* 518 (Pt 1):257-269.
33. Streutker, C. J., Huizinga, J. D., Campbell, F., Ho, J., and Riddell, R. H. 2003. Loss of CD117 (c-kit)- and CD34-positive ICC and associated CD34-positive fibroblasts defines a subpopulation of chronic intestinal pseudoobstruction. *Am J Surg Pathol* 27:228-235.
34. Vanderwinden, J. M., Liu, H., De Laet, M. H., and Vanderhaeghen, J. J. 1996. Study of the interstitial cells of Cajal in infantile hypertrophic pyloric stenosis. *Gastroenterology* 111:279-288.
35. Ordog, T., Takayama, I., Cheung, W. K., Ward, S. M., and Sanders, K. M. 2000. Remodeling of networks of interstitial cells of Cajal in a murine model of diabetic gastroparesis. *Diabetes* 49:1731-1739.
36. Bassotti, G., Villanacci, V., Maurer, C. A., Fisogni, S., Di Fabio, F., Cadei, M., Morelli, A., Panagiotis, T., Cathomas, G., and Salerni, B. 2006. The role of glial cells and apoptosis of enteric neurones in the neuropathology of intractable slow transit constipation. *Gut* 55:41-46.
37. Torihashi, S., Ward, S. M., Nishikawa, S., Nishi, K., Kobayashi, S., and Sanders, K. M. 1995. c-kit-dependent development of interstitial cells and electrical activity in the murine gastrointestinal tract. *Cell Tissue Res* 280:97-111.
38. Neal, K. R., Hebden, J., and Spiller, R. 1997. Prevalence of gastrointestinal symptoms six months after bacterial gastroenteritis and risk factors for development of the irritable bowel syndrome: postal survey of patients. *BMJ* 314:779-782.
39. Thornley, J. P., Jenkins, D., Neal, K., Wright, T., Brough, J., and Spiller, R. C. 2001. Relationship of *Campylobacter* toxigenicity in vitro to the development of postinfectious irritable bowel syndrome. *J Infect Dis* 184:606-609.
40. Gwee, K. A. 2005. Irritable bowel syndrome in developing countries—a disorder of civilization or colonization? *Neurogastroenterol Motil* 17:317-324.
41. Dunlop, S. P., Jenkins, D., Neal, K. R., Naesdal, J., Borgaonker, M., Collins, S. M., and Spiller, R. C. 2003. Randomized, double-blind, placebo-controlled trial of prednisolone in post-infectious irritable bowel syndrome. *Aliment Pharmacol Ther* 18:77-84.
42. Barbara, G., Stanghellini, V., Cremon, C., De Giorgio, R., Fronzoni, L., Serra, M., and Corinaldesi, R. 2009. Aminosalicylates and other anti-inflammatory compounds for irritable bowel syndrome. *Dig Dis* 27 Suppl 1:115-121.
43. Dorofeyev, A. E., Kiriyan, E. A., Vasilenko, I. V., Rassokhina, O. A., and Elin, A. F. 2011. Clinical, endoscopical and morphological efficacy of mesalazine in patients with irritable bowel syndrome. *Clin Exp Gastroenterol* 4:141-153.
44. Spiller, R., and Campbell, E. 2006. Post-infectious irritable bowel syndrome. *Curr Opin Gastroenterol* 22:13-17.
45. O'Sullivan, M., Clayton, N., Breslin, N. P., Harman, I., Bountra, C., McLaren, A., and O'Morain, C. A. 2000. Increased mast cells in the irritable bowel syndrome. *Neurogastroenterol Motil* 12:449-457.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method, comprising:
    providing a biological sample from a subject desiring diagnosis regarding irritable bowel syndrome (IBS);
    detecting in the biological sample, a level of an anti-vinculin antibody, wherein detecting comprises using vinculin, SEQ ID NO:1 or a fragment thereof to detect the anti-vinculin antibody;
    determining a presence or likely presence of IBS if the level of the anti-vinculin antibody is higher than an established control level, or
    determining an absence or likely absence of IBS if the level of the anti-vinculin antibody is equal to or lower than an established control level, wherein the established control level is determined from a group of healthy subjects, a group of subjects with inflammatory bowel disease, or a group of subjects who are either healthy or have inflammatory bowel disease; and
    selecting a therapy for IBS if the presence or likely presence of IBS is determined.

2. The method of claim 1, further comprising administering the therapy.

3. A system for diagnosing irritable bowel syndrome, comprising:
    an isolated biological sample from a subject desiring diagnosis regarding irritable bowel syndrome (IBS); and
    an assay for detecting in the biological sample, a level of an anti-vinculin antibody.

4. The system of claim 3, wherein the assay is an enzyme-linked immunosorbent assay (ELISA), wherein the ELISA comprises using vinculin, SEQ ID NO:1 or a fragment thereof as a substrate or reagent to bind the anti-vinculin antibody.

5. A method, comprising:
    providing a biological sample from a subject desiring to distinguish between irritable bowel syndrome (IBS) and inflammatory bowel disease (IBD);
    detecting in the biological sample, a level of an anti-vinculin antibody, wherein detecting comprises using vinculin, SEQ ID NO:1 or a fragment thereof to detect the anti-vinculin antibody; and
    determining a presence or likely presence of IBS, and an absence or likely absence of IBD if the level of the anti-vinculin antibody is higher than an established control level; and
    selecting a therapy for IBS if the presence or likely presence of IBS is determined.

6. The method of claim 5, wherein the IBS therapy comprises a course of antibiotic therapy.

7. The method of claim 5, wherein the therapy comprises talin, f-actin, a-catenin or a combination thereof.

8. The method of claim 5, further comprising administering the IBS therapy.

9. A system, comprising:
    an isolated biological sample from a subject desiring a diagnosis to distinguish between irritable bowel syndrome (IBS) and inflammatory bowel disease (IBD); and
    an assay for detecting in the biological sample, a level of an anti-vinculin antibody.

10. The system of claim 9, wherein the assay is an enzyme-linked immunosorbent assay (ELISA), wherein the ELISA comprises using vinculin, SEQ ID NO:1 or a fragment thereof as a substrate or reagent to bind the anti-vinculin antibody.

11. The method of claim 1, wherein the therapy comprises talin, f-actin, a-catenin or a combination thereof.

12. The method of claim 1, wherein the therapy comprises a course of antibiotic therapy.

* * * * *